United States Patent [19]

Whitfeld et al.

[11] Patent Number: 5,298,400
[45] Date of Patent: Mar. 29, 1994

[54] POLYNUCLEOTIDE CONSTRUCTS FOR SECRETED GLYCOSYLATED PLASMINOGEN ACTIVATOR INHIBITOR-2 (PAI-2)

[75] Inventors: Peter L. Whitfeld, Glebe; Michael A. Richardson, Belrose; Clive L. Bunn, West Ryde, all of Australia

[73] Assignee: Biotechnology Australia Pty. Ltd., New South Wales, Australia

[21] Appl. No.: 679,052
[22] PCT Filed: Sep. 4, 1990
[86] PCT No.: PCT/AU90/00396
§ 371 Date: May 6, 1991
§ 102(e) Date: May 6, 1991
[87] PCT Pub. No.: WO91/03556
PCT Pub. Date: Mar. 21, 1991

[30] Foreign Application Priority Data

Sep. 5, 1989 [AU] Australia .................. PJ6179

[51] Int. Cl.$^5$ ............ C12N 15/15; C12N 15/03; C12N 15/06; C12P 21/02
[52] U.S. Cl. ................... 435/69.8; 435/69.2; 435/172.3; 435/240.1; 435/240.2; 435/320.1
[58] Field of Search ............... 536/27, 23.5; 435/320.1, 69.2, 69.8, 240.1, 240.2, 172.3; 935/48

[56] References Cited

U.S. PATENT DOCUMENTS 4,546,082  10/1985  Kurjan et al. .................. 435/172.3

FOREIGN PATENT DOCUMENTS

| 0278696 | 8/1988 | European Pat. Off. |
| 278696 | 8/1988 | European Pat. Off. |
| 3713272 | 11/1988 | Fed. Rep. of Germany |
| 3722673A1 | 1/1989 | Fed. Rep. of Germany |
| 2611723 | 9/1988 | France |
| 63-233789 | 9/1988 | Japan |
| 85/00191 | 3/1986 | World Int. Prop. O. |
| 87/00068 | 9/1987 | World Int. Prop. O. |
| WO87/05628 | 9/1987 | World Int. Prop. O. |
| WO87/06590 | 11/1987 | World Int. Prop. O. |

OTHER PUBLICATIONS

Leicht et al., "Sequence homology and structural comparison . . . " Nature 297 pp. 655-659, 1982.
Luckow et al., "Trends in the Development of Baculovirus Expression Vectors", Bio/Technology, 6: 47-55 (1988).
Bishop et al., "Baculovirus Expression Vectors", Advances in Gene Technology, 1:55-72 (1990).
Fraser, "Expression of Eucaryotic Genes in Insect Cell Cultures", In Vitro Cellular & Developmental Biology, 25(3), Part 1, 225-235 (1989).
R. Ye, et al., "Mammalian Protein Secretion Without Signal Peptide Removal", Journal of Biological Chemistry, vol. 263, No. 10, 1988, pp. 4869-4875.
R. Ye, et al., "cDNA Cloning and Expression in Escherichia coli of a Plasminogin Activator Inhibitor from Human Placenta", Journal of Biological Chemistry, vol. 262, No. 8, 1987, pp. 3718-3725.
E. Lawrence, "Henderson's Dictionary of Biological Terms", 10th edition, 1989, p. 315.
S. Ali, et al., "Characterisation of the Alleles encoding ovine β-lactoglobulins A and B", GENE, vol. 19, 1990, pp. 201-207.

(List continued on next page.)

Primary Examiner—Robert J. Hill, Jr.
Assistant Examiner—Marianne Porta Allen
Attorney, Agent, or Firm—Foley & Lardner

[57] ABSTRACT

This invention relates to PAI-2 and its expression as a recombinant molecule in eukaryotic cell lines as a glycosylated secreted molecule, to the constructs expressing it, to host cells expressing it, to compositions comprising it, to methods of treatment, prophylaxis and diagnosis using it and to antibodies raised against it. The invention also provides a 414 amino acid form of PAI-2 wherein the N-terminal methionine residue is deleted, a 60 kD glycosylated secreted recombinant form of PAI-2 and compositions and methods using these molecules. The invention further relates to a novel synthetic signal peptide.

11 Claims, 19 Drawing Sheets

OTHER PUBLICATIONS

Antalis et al., "Cloning and expression of a cDNA coding for a human monocyte-derived plasminogen activator inhibitor", *Proc. Natl. Acad. Sci. USA*, 85: 985–989 (1988).

Barsoum "Introduction of Stable High-Copy-Number DNA into Chinese Hamster Ovary Cells by Electroporation", *DNA And Cell Biology* 9(4): 293–300 (1990).

Beck et al. "Nucleotide Sequence and Exact Localization Of The Neomycin Phosphotransferase Gene From Transposon Tn5", *Gene*, 19: 327–336 (1982).

Belin et al. "Differential Targeting Of Two Forms Of Plasminogen Activator . . . ", Abst. of 2nd Int'l Workshop on Molecular & Cellular Biol. of Plasminogen Activation, Brookhaven Ntl. Lab., Long Island, N.Y. (Apr. 1989).

Belin et al. "Facultative Polypeptide Translocation Allows A Single mRNA To Encode The Secreted And Cytosolic Forms Of Plasminogen Activators Inhibitor 2", *The EMBO Journal*, 8(11): 3287–3294 (1989).

Birnboim et al. "A Rapid Alkaline Extraction Procedure For Screening Recombinant Plasmid DNA", *Nucleic Acids Research*, 7(6): 1513–1523 (1979).

Botterman et al. "High-level Production of the EcoRI Endonuclease Under The Control of the PL Promotor Of Bacteriophage Lambda", *Gene*, 37: 229–239 (1985).

Coleman et al. "A Coupled Photometric Assay for Plasminogen Activator", *Methods in Enzymology*, 80: 408–414 (1981).

Freshney "Cloning and Selection of Specific Cell Types", *Culture of Animal Cells*, 137–139.

Genton et al. "Phorbol Ester Induces The Biosynthesis Of Glycosylated And Nonglycosylated Plasminogen Activator Inhibitor 2 . . . ", *J. Cell. Biol.*, 104: 705–712 (1987).

Gottesman et al. "Transcription Antitermination Of Bacteriophage Lambda N Gene Product", *J. Mol. Biol.*, 140: 57–75 (1980).

Hanahan "Techniques for Transformation of *E. Coli*", *DNA Cloning*, vol. 1: 109–135.

Hiebert et al. "Cell Surface Expression of Glycosylated, Nonglycosylated, and Truncated Forms of a Cytoplasmic Protein Pyruvate Kinase", *J. Cell. Biol.* 107: 865–876 (1988).

Kruithof et al. "Purification and Characterization of a Plasminogen Activator Inhibitor from the Histiocytic Lymphoma Cell Line U-937", *J. Biol. Chem.*, 261: 24: 11207–11213 (1986).

Lecander et al. "Isolation of a New Specific Plasminogen Activator Inhibitor From Pregnancy Plasma", *British J. Haematology*, 62: 221–228 (1986).

Maeda et al. "Production Of Human α-Interferon in Silkworm Using A Baculovirus Vector", *Nature*, 315: 592–594 (1985).

Matsudaira "Sequence from Picomole Quantities of Proteins Electroblotted Onto Polyvinylidene Difluoride Membranes", *J. Biol. Chem.*, 262(21): 10035–10038 (1987).

Medcalf et al. "Gluocorticoid-modulated Gene Expression of Tissue-and Urinary-type Plasminogen . . . ", *J. Cell. Biol.*, 106: 971–978 (1988).

Morein et al. "Iscom, a Novel Structure for Antigenic Presentation of Membrane Proteins from Enveloped Viruses" *Nature*, 308: 457–460 (1984).

Ny et al. "Plasminogen Activator Inhibitor Type 2 cDNA Transfected Into Chinese Hamster Ovary Cells . . . ", *Fibrinolysis*, 189–196 (1989).

Ny et al. "Expression of PAI–2 In Eucaryotic Cells", *Fibinolysis Abstract*, vol. 2 Supp. 1:21 p. 11 (1988).

Raetz et al. "Somatic Cell Cloning in Polyester Stacks", *Proc. Natl. Acad. Sci. USA*, 79: 3223–3227 (1982).

Soberon et al. "Construction and Characterization of New Cloning Vehicles", *Gene*, 9: 287–305 (1980).

Spandidos et al. "Expression of Exogenous DNA in Mammalian Cells", *Transcription and Translation–A Practical Approach*, 1–48.

Speicher "Microsequencing with PVDF Membranes: Efficient Electroblotting . . . ", *Techniques in Protein Chemistry*, 24–35.

Subramani et al., "Expression of the Mouse Dihydrofolate Reductase Complementary Deoxyribonucleic Acid . . . ", *Molecular and Cellular Biol.*, 1(9): 854–864 (1981).

Urlaub et al., "Isolation of Chinese Hamster Cell Mutants Deficient In Dihydrofolate Reductase Activity", *Proc. Natl. Acad. Sci. USA*, 77(7): 4216–4220 (1980).

Urlaub "Effect of Gamma Rays at the Dihydrofolate Reductase Locus: Deletions and Inversion", *Somatic Cell and Molecular Genetics*, 12(6): 555–566 (1986).

von Heijne "A New Method For Predicting Signal Sequence Cleavage Sites", *Nucleic Acids Research*, 14(11): 4683–4690 (1986).

Yanisch-Perron et al. "Improved M13 Phage Cloning Vectors and Host Strains: Nucleotide Sequences of the M13mp18 . . . ", *Gene*, 33: 103–119 (1985).

Zettlmeissl et al. "Expression of Biologically Active Human Antithrombin III In Chinese Hamster Ovary Cells", *Biotechnology*, 5: 720–725 (1987).

Ye et al. "Structure of the Gene for Human Plasminogen Activator Inhibitor-2", *J. Biological Chem.* 264(1): 5495–5502 (1989).

FIG. I

FIG. I - adaptor for cloning native PAI-2 gene into expression vectors

OLIGO A1 (20mer) - adaptor for cloning native PAI-2 gene into expression vectors

5' AGCTTGTCGACACCATGGAA 3'
                    M  E

OLIGO A2 (20 mer) - complementary to A1

5' GATCTTCCATGGTGTCGACA 3'

OLIGO B1 (77mer) - encodes synthetic signal peptide and signal peptidase recognition site 5' AGCTTGTCGACACCATGAAATGTCTGCTCGCTCTCGGTCTGCTAGCTTTCGTGCCTTGTGCTGAGGGCTATGGAA 3'
                    M  K  C  L  L  A  L  G  L  L  A  F  V  P  L  V  R  A  M  E OLIGO B2 (77mer) - complementary to B1

5' GATCTTCCATAGCCCTCACCAACGGCACGAAAGCTAGCAGACCGAGAGCGAGCAGACATTTCATGGTGTCGACA 3'

OLIGO C1 (89mer) - encodes alpha -1- antitrypsin signal and signal peptidase cleavage site 5' AGCTTGTCGACACCATGCCTTCTTCTGTCTCTTGGGGCATCCTGCTGTTGGCCGGCCTGTGTTGCCTGGTCCCTGTCTCTCTGGCTGAA 3'
                    M  P  S  S  V  S  W  G  I  L  L  L  A  G  L  C  C  L  V  P  V  S  L  A  E OLIGO C2 (89mer) - complementary to C1

5' GATCTTCAGCCAGAGAGACAGGGACCAGGCAACACAGGCCTGCTAGCAGGATGCCCCAAGAGACAGAAGAAGGCATGGTGTCGACA 3'

FIG. 2B cont.'
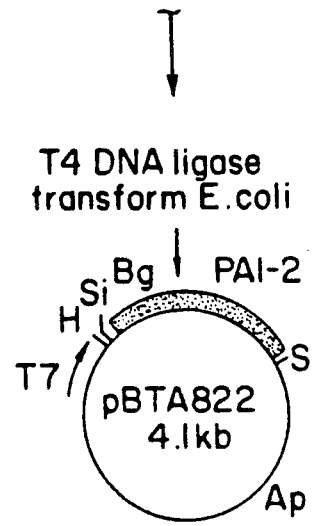
ABBREVIATIONS:
PROMOTERS
PL  – LAMBDA PL
T7  – T7 RNA POLYMERASE
SP6 – SP6 RNA POLYMERASE
SVE – SV40 EARLY
SVL – SV40 LATE
RESTRICTION SITES
BG – BGL II
E  – ECOR I
H  – HIND III
P  – PSTI
S  – SACI
SI – SALI
X  – XHOI
AP   – AMPICILLIN RESISTANCE GENE
DHFR – DIHYDROFOLATE REDUCTASE GENE
NEO  – G418/KANAMYCIN RESISTANCE GENE
MCS  – MULTI-CLONING SITE
T/PA – SV40 T INTRON AND POLYADENYLATION SIGNALS

ABBREVIATIONS:

PROMOTERS

PL — LAMBDA PL
T7 — T7 RNA POLYMERASE
SP6 — SP6 RNA POLYMERASE
SVE — SV40 EARLY
SVL — SV40 LATE

RESTRICTION SITES

BG — BGL II
E — ECOR I
H — HIND III
P — PST I
S — SAC I
SI — SAL I
X — XHO I

AP — AMPICILLIN RESISTANCE GENE
DHFR — DIHYDROFOLATE REDUCTASE GENE
NEO — G418/KANAMYCIN RESISTANCE GENE
MCS — MULTI-CLONING SITE
T/PA — SV40 T INTRON AND POLYADENYLATION SIGNALS

FIG. 6
Urokinase Binding: Medium
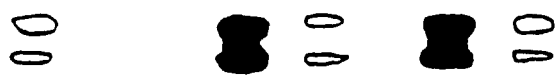
92kDa -
69kDa -
46kDa -
30kDa -

| Pos | 1 | 2 | 3 | 4 | 5 | 6 | 7 | 8 | 9 | 10 | 11 | 12 | 13 | 14 | 15 | 16 | 17 | 18 | End |
|---|---|---|---|---|---|---|---|---|---|---|---|---|---|---|---|---|---|---|---|
| 677 | TTA Leu | CCT Pro | GAA Glu | GGT Gly | TCT Ser | GTA Val | GAT Asp | GGG Gly | GAT Asp | ACC Thr | AGG Arg | ATG Met | CTC Val | CTG Leu | GTC Val | AAT Asn | GCT Ala | GTC Val | 731 |
| | TAC Tyr | TTC Phe | AAA Lys | GGA Gly | AAG Lys | TGG Trp | AAA Lys | ACT Thr | TTT Phe | ACA Thr | GAG Glu | AAG Lys | AAA Lys | CTA Leu | AAT Asn | GGC Gly | CTT Leu | TAT Tyr | 785 |
| | CCT Pro | TTC Phe | CGT Arg | GTA Val | AAC Asn | TCG Ser | GCT Ala | CAG Gln | ACA Thr | CGC Arg | CCT Pro | GTA Val | ATG Met | ATG Met | TAC Tyr | TTC Phe | TTC Phe | CGT Arg | 839 |
| | GAA Glu | AAG Lys | CTA Leu | AAC Asn | ATT Ile | GGA Gly | TAC Tyr | ATA Ile | GAC Asp | GAA Glu | CTA Leu | AAG Lys | CAG Gln | ATG Met | AAG Lys | CTA Leu | GAA Glu | CTC Leu | 893 |
| | CCA Pro | TAT Tyr | GCT Ala | CAT His | GAT Asp | GTT Val | ATG Met | AGT Ser | TTC Phe | TTG Leu | TTC Leu | CTT Leu | CCA Pro | ACC Thr | CTT Leu | ATT Ile | GCC Ala | GAT Asp | 947 |
| | GTG Val | TCC Ser | ACT Thr | GGC Gly | ATG Met | GAG Glu | CTC Leu | GAA Glu | GAT Asp | GAA Glu | GAA Glu | GAG Glu | GTT Val | GAA Glu | GAC Asp | AAA Lys | CTC Leu | AAC Asn | 1001 |
| | AAG Lys | TGG Trp | AGC Ser | AAA Lys | ATG Met | AAT Asn | TAT Tyr | TAT Tyr | GAT Asp | AGA Arg | TCA Ser | TTC Phe | ACC Thr | GAC Asp | GTA Val | TAC Tyr | ATA Ile | CCC Pro | 1055 |
| | CAG Gln | TTC Phe | TTA Leu | GAC Asp | GGC Gly | TAT Tyr | GGA Gly | GCT Ala | GAA Glu | AAT Asn | TTC Phe | GCC Ala | GGG Gly | GGG Gly | AGA Arg | ACC Ser | ATG Met | GGC Gly | 1109 |
| | ATG Met | GAG Glu | CTT Leu | GAC Asp | GCC Ala | AAG Lys | GGA Gly | GTC Val | CGG Arg | CAA Gln | GCC Ala | ATG Met | GTG Val | GAT Asp | TCG Ser | GTG Val | GAG Glu | AGG Arg | 1163 |
| | AAT Asn | GAC Asp | CTG Leu | TTT Phe | CCC Ala | GAA Glu | GCT Ala | GGC Gly | TTC Phe | GCT Ala | GTT Val | ATG Met | ACA Thr | TTT Phe | GAT Asp | AGA Arg | ATT Ile | AAT Asn | 1217 |
| | GAG Glu | GGC Gly | ACT Thr | GCA Ala | CCC Ala | GTT Val | CAT His | GCT Ala | ACA Thr | GCA Ala | GCT Ala | TTT Phe | ACA Thr | CTT Leu | GGG Gly | CTT Leu | ACT Thr | GGA Gly | 1271 |
| | CAT His | GCA Gly | GCC Gly | CCA Pro | AAC Asn | TGC Cys | ATT Ile | TTA Leu | TTT Phe | AGA Arg | TTT Phe | TCA Ser | TTT Phe | CCC Pro | AGA Arg | ATT Ile | ATG Met | CAT His | 1320 |

TAAAACTAAGCG

FIG. 8

| | | | | | | | | | | | | | | | |
|---|---|---|---|---|---|---|---|---|---|---|---|---|---|---|---|
| | | | | | | AGCTTCTCGACACC | ATG MET | CCT PRO | TCT SER | TCT SER | GTC VAL | TCT SER | TGG TRP | GGC GLY | 41 ATC ILE |
| CTG LEU | CTG LEU | CTA LEU | GCA ALA | GGC GLY | CTG LEU | TGT CYS | GTG VAL | GCA ALA | AAC ASN | ACA THR | CTC LEU | TGT CYS | CTC LEU | GTC VAL | CTC LEU | CCT PRO | GTC VAL | TCT SER | GCT ALA | GAT ASP | 95 CTT Leu |
| TGT Cys | GTG Val | GCA Ala | AAC Asn | ACA Thr | CTC Leu | TTT Phe | GCC Ala | AAC Asn | CAG Gln | ATG Met | CTC Leu | CTC Leu | CTC Leu | CAT His | TTC Phe | TTA Leu | AAT Asn | AAG Lys | CTG Leu | AAA Lys | 149 GCA Ala |
| AGC Ser | CCC Pro | ACC Thr | CAG Gln | AAC Asn | CTC Leu | TTC Phe | CTC Leu | CTC Leu | TCC Ser | CAT His | TCC Ser | AGC Ser | ATC Ile | AGC Ser | TCG Ser | TGG Trp | CCA Pro | AAG Lys | ACC Thr | ATG Met | 203 GCA Ala |
| ATG Met | GTC Val | TAC Tyr | ATG Met | CAG Gln | TCC Ser | AGG Arg | CTC Leu | GGC Gly | AGC Ser | AGC Ser | AGC Ser | GAC Asp | GCA Ala | GAA Glu | ACC Thr | AAG Lys | AGC Ser | ATG Met | AGG Arg | AAG Lys | 257 GCC Ala |
| CAG Gln | TTT Phe | AAT Asn | GAA Glu | GGG Gly | GGA Gly | GCC Ala | AAT Asn | GCC Ala | ATG Met | GCA Ala | GAT Asp | GAA Glu | GCA Ala | ACC Thr | AAG Lys | GAG Glu | CAG Gln | ACT Thr | AAC Asn | GTG Val | 311 CTT Leu |
| ACC Thr | AGC Ser | TGT Cys | GGG Gly | ATG Met | CTG Leu | CAG Gln | CAT His | ATC Ile | ATC Ile | CAG Gln | ATG Met | CCC Pro | ATG Met | CAG Gln | TAT Tyr | CCT Pro | AGT Ser | TAT Tyr | CGC Arg | AAC Asn | 365 TTT Phe |
| TTG Leu | CAG Gln | GCA Ala | CAA Gln | GCA Ala | ACA Thr | GAT Asp | ATC Ile | ATC Ile | CAT His | CAT His | ATC Ile | GGT Gly | TCA Ser | TCT Ser | AGT Ser | CTT Leu | TCT Ser | AGT Ser | TTC Phe | AGT Ser | 419 ATT Ile |
| GCA Ala | ATC Ile | GCA Ala | GCA Ala | ACA Thr | AGC Ser | GGG Gly | TAT Tyr | TAT Tyr | TTA Leu | TTA Leu | TAT Tyr | TCC Ser | CTG Leu | AAT Asn | CGA Arg | CCT Pro | TCT Ser | CGA Arg | CGC Arg | AGT Ser | 473 TCT Ser |
| GGT Gly | GAG Glu | AAG Lys | TCT Ser | GCC Ala | AGC Ser | TTC Phe | GAA Glu | AAT Asn | GAA Glu | GAA Glu | GAA Glu | GAA Glu | TAT Tyr | TGT Cys | TGT Cys | GAT Asp | AAT Asn | AAG Lys | CTG Leu | AAA Lys | 527 TTT Phe |
| TAC Tyr | TCC Ser | TCA Ser | GAA Glu | CCC Pro | CAG Gln | GCA Ala | GAC Asp | TTC Phe | TTC Phe | CTA Leu | CTA Leu | TCG Ser | TGC Cys | GAA Glu | GCA Ala | CTC Leu | CAG Gln | GAA Glu | AAA Lys | GCT Ala | 581 TAT Tyr |
| AAA Lys | AAG Lys | ATT Ile | AAT Asn | TCC Ser | TGG Trp | GTC Val | ACT Thr | CAA Gln | CAA Gln | ACC Thr | ACC Thr | GGC Gly | AAA Lys | AAA Lys | AAA Lys | CCA Pro | ATC Ile | GAA Glu | AAA Lys | AAC Asn | 635 AGA Arg |
| | | | | | | | | | | | | | | | | | | | | | TTG Leu |

FIG. 8 CONT.

| | | | | | | | | | | | 689<br>GTC<br>Val<br>743 |
|---|---|---|---|---|---|---|---|---|---|---|---|
| TTA<br>Leu | CCT<br>Pro | GAA<br>Glu | GGT<br>Gly | TCT<br>Ser | GTA<br>Val | GAT<br>Asp | GGG<br>Gly | GAT<br>Asp | ACC<br>Thr | AGG<br>Arg | ATG<br>Met | GTC<br>Val | CTG<br>Leu | GTG<br>Val | AAT<br>Asn | GCT<br>Ala | TAT<br>Tyr<br>797 |
| TAC<br>Tyr | TTC<br>Phe | AAA<br>Lys | GGA<br>Gly | AAG<br>Lys | TGG<br>Trp | AAA<br>Lys | ACT<br>Thr | CCA<br>Pro | TTT<br>Phe | GAG<br>Glu | AAA<br>Lys | AAA<br>Lys | CTA<br>Leu | AAT<br>Asn | GGG<br>Gly | CTT<br>Leu | CCT<br>Pro<br>851 |
| CCT<br>Pro | TTC<br>Phe | CCT<br>Arg | GTA<br>Val | AAC<br>Asn | TCG<br>Ser | GCT<br>Ala | CAG<br>Gln | CCC<br>Arg | ACA<br>Thr | CCT<br>Pro | GTA<br>Val | CAG<br>Gln | ATG<br>Met | ATG<br>Met | TAC<br>Tyr | TTG<br>Leu | AGG<br>Arg<br>905 |
| GAA<br>Glu | AAG<br>Lys | CTA<br>Leu | AAC<br>Asn | ATT<br>Ile | GGA<br>Gly | TAC<br>Tyr | ATA<br>Ile | CAG<br>Gln | GAC<br>Asp | GAA<br>Glu | AAG<br>Lys | ATG<br>Met | CAG<br>Gln | ATT<br>Ile | CTA<br>Leu | GAA<br>Glu | CTC<br>Leu<br>959 |
| CCA<br>Pro | TAT<br>Tyr | CTA<br>Leu | GGA<br>Gly | GAT<br>Asp | GCA<br>Ala | AGC<br>Ser | ATG<br>Met | CTG<br>Leu | TTC<br>Phe | TTG<br>Leu | CTT<br>Leu | ATA<br>Ile | GAT<br>Asp | CCA<br>Pro | CAG<br>Gln | GCC<br>Ala | GAT<br>Asp<br>1013 |
| GTG<br>Val | TCC<br>Ser | ACT<br>Thr | GGC<br>Gly | CTG<br>Leu | GAG<br>Glu | GGA<br>Gly | CAT<br>His | CAG<br>Gln | ACT<br>Ser | GAA<br>Glu | ATA<br>Ile | GAA<br>Glu | TAT<br>Tyr | ACC<br>Thr | GAC<br>Asp | CTC<br>Leu | AAC<br>Asn<br>1067 |
| AAG<br>Lys | TGG<br>Trp | ACC<br>Thr | AGC<br>Ser | AAA<br>Lys | GAC<br>Asp | AAG<br>Lys | ATG<br>Met | ATG<br>Met | GAT<br>Asp | AGA<br>Arg | TCC<br>Ser | GTT<br>Val | GAG<br>Glu | TCC<br>Ser | AGA<br>Arg | ATG<br>Met | GGC<br>Gly<br>1121 |
| CAG<br>Gln | TTC<br>Phe | AAA<br>Lys | GAC<br>Asp | GAA<br>Glu | GAC<br>Asp | CAT<br>His | TAT<br>Tyr | GGA<br>Gly | AAT<br>Asn | TTC<br>Phe | ATT<br>Ile | TTC<br>Phe | CTG<br>Leu | ATG<br>Met | TCG<br>Ser | GAG<br>Glu | AGG<br>Arg<br>1175 |
| ATG<br>Met | GAG<br>Glu | GAC<br>Asp | CCC<br>Ala | CTT<br>Leu | AAC<br>Asn | AAG<br>Lys | GGA<br>Gly | GTG<br>Val | GCC<br>Ala | CAA<br>Gln | GCC<br>Ala | GCC<br>Ala | CTC<br>Leu | GAT<br>Asp | GGG<br>Gly | GAT<br>Asp | GAG<br>Glu<br>1229 |
| AAT<br>Asn | GAC<br>Asp | ACT<br>Thr | TTT<br>Phe | CTT<br>Leu | CCC<br>Ala | CCT<br>Ala | GTG<br>Val | GCA<br>Ala | ACA<br>Thr | TTC<br>Phe | GTT<br>Val | TTT<br>Phe | CTT<br>Leu | GGG<br>Gly | AGA<br>Arg | ACT<br>Thr | GGA<br>Gly<br>1283 |
| CAT<br>His | GGA<br>Gly | GGC<br>Gly | CCA<br>Pro | CAG<br>Gln | TTT<br>Phe | GTC<br>Val | GCA<br>Ala | GAT<br>Asp | CAT<br>His | CCT<br>Pro | TTT<br>Phe | CTT<br>Leu | ATT<br>Ile | TTT<br>Phe | ATT<br>Ile | ATG<br>Met | CAT<br>His<br>1340 |
| AAG<br>Lys | ATA<br>Ile | ACC<br>Thr | AAC<br>Asn | TGC<br>Cys | ATT<br>Ile | TTA<br>Leu | GGC<br>Gly | TTT<br>Phe | AGA<br>Arg | TTT<br>Phe | TCA<br>Ser | CCC<br>Pro | ATT<br>Ile | ACT<br>Thr | | | TAAAACTAAGCG |

Glycosidase Digestion of 60,000 Mr PAI-2

ABBREVIATIONS: H - ENDOGLYCOSIDASE H
F - GLYCOPEPTIDASE F
N - NEURAMINIDASE
O - O-GLYCANASE
B - NON-GLYCOSYLATED PAI-2

N-Terminal Analysis of 60,000 Mr PAI-2 Secreted from COS cells transfected with pBTA825 and pBTA826

N-Terminal Analysis of 60,000 Mr PAI-2 Secreted from COS cells transfected with pBTA825 and pBTA826

FIG. 11

Secretion of PAI-2 into Medium from Transfected CHO-KI Cells

|  | transfected plasmid | |
|---|---|---|
| Markers (kDa) | pBTA827 vector + PAI-2 gene | pBTA830 vector only |
| 92 - | | |
| 69 - | ▬ | |
| 46 - | — | |
| 30 - | | |

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 19 amino acids
      ( B ) TYPE: amino acid
      ( D ) TOPOLOGY: unknown ( i i ) MOLECULE TYPE: peptide ( i x ) FEATURE:
      ( A ) NAME/KEY: Peptide
      ( B ) LOCATION: 1..19
      ( D ) OTHER INFORMATION: /note="Synthetic signal peptide"

( x i ) SEQUENCE DESCRIPTION: SEQ ID NO:1:

```
Met Lys Cys Leu Leu Leu Ala Leu Gly Leu Leu Ala Phe Val Pro Leu
 1               5                  10                  15
Val Arg Ala
```

( 2 ) INFORMATION FOR SEQ ID NO:2:

( i ) SEQUENCE CHARACTERISTICS:
    ( A ) LENGTH: 24 amino acids
    ( B ) TYPE: amino acid
    ( D ) TOPOLOGY: unknown ( i i ) MOLECULE TYPE: peptide ( i x ) FEATURE:
    ( A ) NAME/KEY: Peptide
    ( B ) LOCATION: 1..24
    ( D ) OTHER INFORMATION: /note="Signal peptide from human
        a-1- antitrypsin"

( x i ) SEQUENCE DESCRIPTION: SEQ ID NO:2:

```
Met Pro Ser Ser Val Ser Trp Gly Ile Leu Leu Leu Ala Gly Leu Cys
1               5                   10                  15

Cys Leu Val Pro Val Ser Leu Ala
                20
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

GATCTNNNNN NNNNNNNNNN NATGGAG                      27

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:4:

GGCCCATATG ATATCTCGAG ACTAGTC                      27

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonculeotide ( i x ) FEATURE:
        ( A ) NAME/KEY: CDS
        ( B ) LOCATION: 15..20

( x i ) SEQUENCE DESCRIPTION: SEQ ID NO:5:

```
AGCTTGTCGA CACC ATG GAA                                         20
              Met Glu
               1
```

( 2 ) INFORMATION FOR SEQ ID NO:6:

( i ) SEQUENCE CHARACTERISTICS:
        ( A ) LENGTH: 2 amino acids (B) TYPE: amino acid
(D) TOPOLOGY: linear (ii) MOLECULE TYPE: protein (xi) SEQUENCE DESCRIPTION: SEQ ID NO:6:

Met Glu
 1

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:7:

GATCTTCCAT GGTGTCGACA     20

(2) INFORMATION FOR SEQ ID NO:8:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (ix) FEATURE:
        (A) NAME/KEY: CDS
        (B) LOCATION: 15..77

(xi) SEQUENCE DESCRIPTION: SEQ ID NO:8:

```
AGCTTGTCGA CACC ATG AAA TGT CTG CTG CTC GCT CTC GGT CTG CTA GCT      50
              Met Lys Cys Leu Leu Leu Ala Leu Gly Leu Leu Ala
               1               5                  10

TTC GTG CCG TTG GTG AGG GCT ATG GAA                                  77
Phe Val Pro Leu Val Arg Ala Met Glu
         15                  20
```

(2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:9:

Met Lys Cys Leu Leu Leu Ala Leu Gly Leu Leu Ala Phe Val Pro Leu
 1               5                  10                  15

Val Arg Ala Met Glu
             20

(2) INFORMATION FOR SEQ ID NO:10:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (i v) ANTI-SENSE: YES (x i) SEQUENCE DESCRIPTION: SEQ ID NO:10:

GATCTTCCAT AGCCCTCACC AACGGCACGA AAGCTAGCAG ACCGAGAGCG AGCAGCAGAC    60

ATTTCATGGT GTCGACA    77

(2) INFORMATION FOR SEQ ID NO:11:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i x) FEATURE:
        (A) NAME/KEY: CDS
        (B) LOCATION: 15..89

(i x) FEATURE:
        (A) NAME/KEY: sigpeptide
        (B) LOCATION: 15..86
        (C) IDENTIFICATION METHOD: experimental
        (D) OTHER INFORMATION: /product="a-1-antitrypsin signal"
            / evidence=EXPERIMENTAL (x i) SEQUENCE DESCRIPTION: SEQ ID NO:11:

```
AGCTTGTCGA CACC ATG CCT TCT TCT GTC TCT TGG GGC ATC CTG CTG CTA        50
              Met Pro Ser Ser Val Ser Trp Gly Ile Leu Leu Leu
               1               5                   10

GCA GGC CTG TGT TGT CTG GTC CCT GTC TCT CTG GCT GAA                    89
Ala Gly Leu Cys Cys Leu Val Pro Val Ser Leu Ala Glu
         15              20                  25
```

(2) INFORMATION FOR SEQ ID NO:12:

(i) SEQUENCE CHARACTERISTICS:
        (A) LENGTH: 25 amino acids
        (B) TYPE: amino acid
        (D) TOPOLOGY: linear (i i) MOLECULE TYPE: protein (x i) SEQUENCE DESCRIPTION: SEQ ID NO:12:

```
Met Pro Ser Ser Val Ser Trp Gly Ile Leu Leu Leu Ala Gly Leu Cys
 1               5                  10                  15
Cys Leu Val Pro Val Ser Leu Ala Glu
             20                  25
```

(2) INFORMATION FOR SEQ ID NO:13:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i v) ANTI-SENSE: YES (x i) SEQUENCE DESCRIPTION: SEQ ID NO:13:

GATCTTCAGC CAGAGAGACA GGGACCAGAC AACACAGGCC TGCTAGCAGC AGGATGCCCC    60

AAGAGACAGA AGAAGGCATG GTGTCGACA    89

( 2 ) INFORMATION FOR SEQ ID NO:14:

( i ) SEQUENCE CHARACTERISTICS:
        ( A ) LENGTH: 1328 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 15..1319

( i x ) FEATURE:
        ( A ) NAME/KEY: sigpeptide
        ( B ) LOCATION: 15..71
        ( D ) OTHER INFORMATION: /product="Synthetic signal peptide"

( x i ) SEQUENCE DESCRIPTION: SEQ ID NO:14:

```
AGCTTGTCGA CACC ATG AAA TGT CTG CTG CTC GCT CTC GGT CTG CTA GCT        50
              Met Lys Cys Leu Leu Leu Ala Leu Gly Leu Leu Ala
                1               5                  10

TTC GTG CCG TTG GTG AGG GCT ATG GAA GAT CTT TGT GTG GCA AAC ACA        98
Phe Val Pro Leu Val Arg Ala Met Glu Asp Leu Cys Val Ala Asn Thr
         15                  20                  25

CTC TTT GCC CTC AAT TTA TTC AAG CAT CTG GCA AAA GCA AGC CCC ACC       146
Leu Phe Ala Leu Asn Leu Phe Lys His Leu Ala Lys Ala Ser Pro Thr
     30                  35                  40

CAG AAC CTC TTC CTC TCC CCA TGG AGC ATC TCG TCC ACC ATG GCC ATG       194
Gln Asn Leu Phe Leu Ser Pro Trp Ser Ile Ser Ser Thr Met Ala Met
 45                  50                  55                  60

GTC TAC ATG GGC TCC AGG GGC AGC ACC GAA GAC CAG ATG GCC AAG GTG       242
Val Tyr Met Gly Ser Arg Gly Ser Thr Glu Asp Gln Met Ala Lys Val
                 65                  70                  75

CTT CAG TTT AAT GAA GTG GGA GCC AAT GCA GTT ACC CCC ATG ACT CCA       290
Leu Gln Phe Asn Glu Val Gly Ala Asn Ala Val Thr Pro Met Thr Pro
             80                  85                  90

GAG AAC TTT ACC AGC TGT GGG TTC ATG CAG CAG ATC CAG AAG GGT AGT       338
Glu Asn Phe Thr Ser Cys Gly Phe Met Gln Gln Ile Gln Lys Gly Ser
         95                 100                 105

TAT CCT GAT GCG ATT TTG CAG GCA CAA GCT GCA GAT AAA ATC CAT TCA       386
Tyr Pro Asp Ala Ile Leu Gln Ala Gln Ala Ala Asp Lys Ile His Ser
    110                 115                 120

TCC TTC CGC TCT CTC AGC TCT GCA ATC AAT GCA TCC ACA GGG AAT TAT       434
Ser Phe Arg Ser Leu Ser Ser Ala Ile Asn Ala Ser Thr Gly Asn Tyr
125                 130                 135                 140

TTA CTG GAA AGT GTC AAT AAG CTG TTT GGT GAG AAG TCT GCG AGC TTC       482
Leu Leu Glu Ser Val Asn Lys Leu Phe Gly Glu Lys Ser Ala Ser Phe
                145                 150                 155

CGG GAA GAA TAT ATT CGA CTC TGT CAG AAA TAT TAC TCC TCA GAA CCC       530
Arg Glu Glu Tyr Ile Arg Leu Cys Gln Lys Tyr Tyr Ser Ser Glu Pro
            160                 165                 170

CAG GCA GTA GAC TTC CTA GAA TGT GCA GAA GAA GCT AGA AAA AAG ATT       578
Gln Ala Val Asp Phe Leu Glu Cys Ala Glu Glu Ala Arg Lys Lys Ile
        175                 180                 185

AAT TCC TGG GTC AAG ACT CAA ACC AAA GGC AAA ATC CCA AAC TTG TTA       626
Asn Ser Trp Val Lys Thr Gln Thr Lys Gly Lys Ile Pro Asn Leu Leu
    190                 195                 200

CCT GAA GGT TCT GTA GAT GGG GAT ACC AGG ATG GTC CTG GTG AAT GCT       674
Pro Glu Gly Ser Val Asp Gly Asp Thr Arg Met Val Leu Val Asn Ala
205                 210                 215                 220

GTC TAC TTC AAA GGA AAG TGG AAA ACT CCA TTT GAG AAG AAA CTA AAT       722
Val Tyr Phe Lys Gly Lys Trp Lys Thr Pro Phe Glu Lys Lys Leu Asn
```

|  |  |  |  |  |  |  | 225 |  |  |  | 230 |  |  |  | 235 |  |  |
|---|---|---|---|---|---|---|---|---|---|---|---|---|---|---|---|---|---|

```
GGG CTT TAT CCT TTC CGT GTA AAC TCG GCT CAG CGC ACA CCT GTA CAG          770
Gly Leu Tyr Pro Phe Arg Val Asn Ser Ala Gln Arg Thr Pro Val Gln
            240             245             250

ATG ATG TAC TTG CGT GAA AAG CTA AAC ATT GGA TAC ATA GAA GAC CTA          818
Met Met Tyr Leu Arg Glu Lys Leu Asn Ile Gly Tyr Ile Glu Asp Leu
            255             260             265

AAG GCT CAG ATT CTA GAA CTC CCA TAT GCT GGA GAT GTT AGC ATG TTC          866
Lys Ala Gln Ile Leu Glu Leu Pro Tyr Ala Gly Asp Val Ser Met Phe
    270             275             280

TTG TTG CTT CCA GAT GAA ATT GCC GAT GTG TCC ACT GGC TTG GAG CTG          914
Leu Leu Leu Pro Asp Glu Ile Ala Asp Val Ser Thr Gly Leu Glu Leu
285             290             295             300

CTG GAA AGT GAA ATA ACC TAT GAC AAA CTC AAC AAG TGG ACC AGC AAA          962
Leu Glu Ser Glu Ile Thr Tyr Asp Lys Leu Asn Lys Trp Thr Ser Lys
                305             310             315

GAC AAA ATG GCT GAA GAT GAA GTT GAG GTA TAC ATA CCC CAG TTC AAA         1010
Asp Lys Met Ala Glu Asp Glu Val Glu Val Tyr Ile Pro Gln Phe Lys
            320             325             330

TTA GAA GAG CAT TAT GAA CTC AGA TCC ATT CTG AGA AGC ATG GGC ATG         1058
Leu Glu Glu His Tyr Glu Leu Arg Ser Ile Leu Arg Ser Met Gly Met
            335             340             345

GAG GAC GCC TTC AAC AAG GGA CGG GCC AAT TTC TCA GGG ATG TCG GAG         1106
Glu Asp Ala Phe Asn Lys Gly Arg Ala Asn Phe Ser Gly Met Ser Glu
350             355             360

AGG AAT GAC CTG TTT CTT TCT GAA GTG TTC CAC CAA GCC ATG GTG GAT         1154
Arg Asn Asp Leu Phe Leu Ser Glu Val Phe His Gln Ala Met Val Asp
365             370             375             380

GTG AAT GAG GAG GGC ACT GAA GCA GCC GCT GGC ACA GGA GGT GTT ATG         1202
Val Asn Glu Glu Gly Thr Glu Ala Ala Ala Gly Thr Gly Gly Val Met
            385             390             395

ACA GGG AGA ACT GGA CAT GGA GGC CCA CAG TTT GTG GCA GAT CAT CCT         1250
Thr Gly Arg Thr Gly His Gly Gly Pro Gln Phe Val Ala Asp His Pro
            400             405             410

TTT CTT TTT CTT ATT ATG CAT AAG ATA ACC AAC TGC ATT TTA TTT TTC         1298
Phe Leu Phe Leu Ile Met His Lys Ile Thr Asn Cys Ile Leu Phe Phe
            415             420             425

GGC AGA TTT TCC TCA CCC TAAAACTAAG CG                                   1328
Gly Arg Phe Ser Ser Pro
430             435
```

( 2 ) INFORMATION FOR SEQ ID NO:15:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Lys Cys Leu Leu Leu Ala Leu Gly Leu Leu Ala Phe Val Pro Leu
 1               5              10              15

Val Arg Ala Met Glu Asp Leu Cys Val Ala Asn Thr Leu Phe Ala Leu
            20              25              30

Asn Leu Phe Lys His Leu Ala Lys Ala Ser Pro Thr Gln Asn Leu Phe
        35              40              45

Leu Ser Pro Trp Ser Ile Ser Ser Thr Met Ala Met Val Tyr Met Gly
    50              55              60

Ser Arg Gly Ser Thr Glu Asp Gln Met Ala Lys Val Leu Gln Phe Asn
65              70              75              80

Glu Val Gly Ala Asn Ala Val Thr Pro Met Thr Pro Glu Asn Phe Thr
```

|     |     |     |     |     | 85  |     |     |     |     | 90  |     |     |     |     | 95  |     |     |
|---|---|---|---|---|---|---|---|---|---|---|---|---|---|---|---|---|---|

Ser Cys Gly Phe Met Gln Gln Ile Gln Lys Gly Ser Tyr Pro Asp Ala
                100                 105                 110

Ile Leu Gln Ala Gln Ala Ala Asp Lys Ile His Ser Ser Phe Arg Ser
            115                 120                 125

Leu Ser Ser Ala Ile Asn Ala Ser Thr Gly Asn Tyr Leu Leu Glu Ser
        130                 135                 140

Val Asn Lys Leu Phe Gly Glu Lys Ser Ala Ser Phe Arg Glu Glu Tyr
145                 150                 155                 160

Ile Arg Leu Cys Gln Lys Tyr Tyr Ser Ser Glu Pro Gln Ala Val Asp
                165                 170                 175

Phe Leu Glu Cys Ala Glu Glu Ala Arg Lys Lys Ile Asn Ser Trp Val
            180                 185                 190

Lys Thr Gln Thr Lys Gly Lys Ile Pro Asn Leu Leu Pro Glu Gly Ser
        195                 200                 205

Val Asp Gly Asp Thr Arg Met Val Leu Val Asn Ala Val Tyr Phe Lys
210                 215                 220

Gly Lys Trp Lys Thr Pro Phe Glu Lys Lys Leu Asn Gly Leu Tyr Pro
225                 230                 235                 240

Phe Arg Val Asn Ser Ala Gln Arg Thr Pro Val Gln Met Met Tyr Leu
                245                 250                 255

Arg Glu Lys Leu Asn Ile Gly Tyr Ile Glu Asp Leu Lys Ala Gln Ile
            260                 265                 270

Leu Glu Leu Pro Tyr Ala Gly Asp Val Ser Met Phe Leu Leu Leu Pro
        275                 280                 285

Asp Glu Ile Ala Asp Val Ser Thr Gly Leu Glu Leu Leu Glu Ser Glu
290                 295                 300

Ile Thr Tyr Asp Lys Leu Asn Lys Trp Thr Ser Lys Asp Lys Met Ala
305                 310                 315                 320

Glu Asp Glu Val Glu Val Tyr Ile Pro Gln Phe Lys Leu Glu Glu His
                325                 330                 335

Tyr Glu Leu Arg Ser Ile Leu Arg Ser Met Gly Met Glu Asp Ala Phe
            340                 345                 350

Asn Lys Gly Arg Ala Asn Phe Ser Gly Met Ser Glu Arg Asn Asp Leu
        355                 360                 365

Phe Leu Ser Glu Val Phe His Gln Ala Met Val Asp Val Asn Glu Glu
370                 375                 380

Gly Thr Glu Ala Ala Ala Gly Thr Gly Gly Val Met Thr Gly Arg Thr
385                 390                 395                 400

Gly His Gly Gly Pro Gln Phe Val Ala Asp His Pro Phe Leu Phe Leu
                405                 410                 415

Ile Met His Lys Ile Thr Asn Cys Ile Leu Phe Phe Gly Arg Phe Ser
            420                 425                 430

Ser Pro ( 2 ) INFORMATION FOR SEQ ID NO:16:

( i ) SEQUENCE CHARACTERISTICS:
        ( A ) LENGTH: 1340 base pairs
        ( B ) TYPE: nucleic acid
        ( C ) STRANDEDNESS: double
        ( D ) TOPOLOGY: linear ( i i ) MOLECULE TYPE: Other nucleic acid:
        ( A ) DESCRIPTION: Synthetic DNA oligonucleotide ( i x ) FEATURE:
        ( A ) NAME/KEY: CDS
        ( B ) LOCATION: 15..1331

( i x ) FEATURE:
    ( A ) NAME/KEY: sigpeptide
    ( B ) LOCATION: 15..86
    ( D ) OTHER INFORMATION: /product="a-1-antitrypsin signal"

( x i ) SEQUENCE DESCRIPTION: SEQ ID NO:16:

```
AGCTTGTCGA CACC ATG CCT TCT TCT GTC TCT TGG GGC ATC CTG CTG CTA            50
              Met Pro Ser Ser Val Ser Trp Gly Ile Leu Leu Leu
               1           5                      10

GCA GGC CTG TGT TGT CTG GTC CCT GTC TCT CTG GCT GAA GAT CTT TGT            98
Ala Gly Leu Cys Cys Leu Val Pro Val Ser Leu Ala Glu Asp Leu Cys
         15              20                  25

GTG GCA AAC ACA CTC TTT GCC CTC AAT TTA TTC AAG CAT CTG GCA AAA           146
Val Ala Asn Thr Leu Phe Ala Leu Asn Leu Phe Lys His Leu Ala Lys
     30              35                  40

GCA AGC CCC ACC CAG AAC CTC TTC CTC TCC CCA TGG AGC ATC TCG TCC           194
Ala Ser Pro Thr Gln Asn Leu Phe Leu Ser Pro Trp Ser Ile Ser Ser
 45              50                  55                      60

ACC ATG GCC ATG GTC TAC ATG GGC TCC AGG GGC AGC ACC GAA GAC CAG           242
Thr Met Ala Met Val Tyr Met Gly Ser Arg Gly Ser Thr Glu Asp Gln
                 65                  70                  75

ATG GCC AAG GTG CTT CAG TTT AAT GAA GTG GGA GCC AAT GCA GTT ACC           290
Met Ala Lys Val Leu Gln Phe Asn Glu Val Gly Ala Asn Ala Val Thr
             80                  85                  90

CCC ATG ACT CCA GAG AAC TTT ACC AGC TGT GGG TTC ATG CAG CAG ATC           338
Pro Met Thr Pro Glu Asn Phe Thr Ser Cys Gly Phe Met Gln Gln Ile
         95                 100                 105

CAG AAG GGT AGT TAT CCT GAT GCG ATT TTG CAG GCA CAA GCT GCA GAT           386
Gln Lys Gly Ser Tyr Pro Asp Ala Ile Leu Gln Ala Gln Ala Ala Asp
     110                 115                 120

AAA ATC CAT TCA TCC TTC CGC TCT CTC AGC TCT GCA ATC AAT GCA TCC           434
Lys Ile His Ser Ser Phe Arg Ser Leu Ser Ser Ala Ile Asn Ala Ser
125                 130                 135                 140

ACA GGG AAT TAT TTA CTG GAA AGT GTC AAT AAG CTG TTT GGT GAG AAG           482
Thr Gly Asn Tyr Leu Leu Glu Ser Val Asn Lys Leu Phe Gly Glu Lys
                 145                 150                 155

TCT GCG AGC TTC CGG GAA GAA TAT ATT CGA CTC TGT CAG AAA TAT TAC           530
Ser Ala Ser Phe Arg Glu Glu Tyr Ile Arg Leu Cys Gln Lys Tyr Tyr
             160                 165                 170

TCC TCA GAA CCC CAG GCA GTA GAC TTC CTA GAA TGT GCA GAA GAA GCT           578
Ser Ser Glu Pro Gln Ala Val Asp Phe Leu Glu Cys Ala Glu Glu Ala
         175                 180                 185

AGA AAA AAG ATT AAT TCC TGG GTC AAG ACT CAA ACC AAA GGC AAA ATC           626
Arg Lys Lys Ile Asn Ser Trp Val Lys Thr Gln Thr Lys Gly Lys Ile
     190                 195                 200

CCA AAC TTG TTA CCT GAA GGT TCT GTA GAT GGG GAT ACC AGG ATG GTC           674
Pro Asn Leu Leu Pro Glu Gly Ser Val Asp Gly Asp Thr Arg Met Val
205                 210                 215                 220

CTG GTG AAT GCT GTC TAC TTC AAA GGA AAG TGG AAA ACT CCA TTT GAG           722
Leu Val Asn Ala Val Tyr Phe Lys Gly Lys Trp Lys Thr Pro Phe Glu
                 225                 230                 235

AAG AAA CTA AAT GGG CTT TAT CCT TTC CGT GTA AAC TCG GCT CAG CGC           770
Lys Lys Leu Asn Gly Leu Tyr Pro Phe Arg Val Asn Ser Ala Gln Arg
             240                 245                 250

ACA CCT GTA CAG ATG ATG TAC TTG CGT GAA AAG CTA AAC ATT GGA TAC           818
Thr Pro Val Gln Met Met Tyr Leu Arg Glu Lys Leu Asn Ile Gly Tyr
         255                 260                 265

ATA GAA GAC CTA AAG GCT CAG ATT CTA GAA CTC CCA TAT GCT GGA GAT           866
Ile Glu Asp Leu Lys Ala Gln Ile Leu Glu Leu Pro Tyr Ala Gly Asp
     270                 275                 280

GTT AGC ATG TTC TTG TTG CTT CCA GAT GAA ATT GCC GAT GTG TCC ACT           914
```

```
Val Ser Met Phe Leu Leu Leu Pro Asp Glu Ile Ala Asp Val Ser Thr
285                 290                 295                 300

GGC TTG GAG CTG CTG GAA AGT GAA ATA ACC TAT GAC AAA CTC AAC AAG    962
Gly Leu Glu Leu Leu Glu Ser Glu Ile Thr Tyr Asp Lys Leu Asn Lys
                    305                 310                 315

TGG ACC AGC AAA GAC AAA ATG GCT GAA GAT GAA GTT GAG GTA TAC ATA   1010
Trp Thr Ser Lys Asp Lys Met Ala Glu Asp Glu Val Glu Val Tyr Ile
                320                 325                 330

CCC CAG TTC AAA TTA GAA GAG CAT TAT GAA CTC AGA TCC ATT CTG AGA   1058
Pro Gln Phe Lys Leu Glu Glu His Tyr Glu Leu Arg Ser Ile Leu Arg
            335                 340                 345

AGC ATG GGC ATG GAG GAC GCC TTC AAC AAG GGA CGG GCC AAT TTC TCA   1106
Ser Met Gly Met Glu Asp Ala Phe Asn Lys Gly Arg Ala Asn Phe Ser
        350                 355                 360

GGG ATG TCG GAG AGG AAT GAC CTG TTT CTT TCT GAA GTG TTC CAC CAA   1154
Gly Met Ser Glu Arg Asn Asp Leu Phe Leu Ser Glu Val Phe His Gln
365                 370                 375                 380

GCC ATG GTG GAT GTG AAT GAG GAG GGC ACT GAA GCA GCC GCT GGC ACA   1202
Ala Met Val Asp Val Asn Glu Glu Gly Thr Glu Ala Ala Ala Gly Thr
                385                 390                 395

GGA GGT GTT ATG ACA GGG AGA ACT GGA CAT GGA GGC CCA CAG TTT GTG   1250
Gly Gly Val Met Thr Gly Arg Thr Gly His Gly Gly Pro Gln Phe Val
                400                 405                 410

GCA GAT CAT CCT TTT CTT TTT CTT ATT ATG CAT AAG ATA ACC AAC TGC   1298
Ala Asp His Pro Phe Leu Phe Leu Ile Met His Lys Ile Thr Asn Cys
            415                 420                 425

ATT TTA TTT TTC GGC AGA TTT TCC TCA CCC TAAAACTAAG CG             1340
Ile Leu Phe Phe Gly Arg Phe Ser Ser Pro
430                 435
```

( 2 ) INFORMATION FOR SEQ ID NO:17:

( i ) SEQUENCE CHARACTERISTICS:
        ( A ) LENGTH: 438 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Pro Ser Ser Val Ser Trp Gly Ile Leu Leu Leu Ala Gly Leu Cys
1                   5                   10                  15

Cys Leu Val Pro Val Ser Leu Ala Glu Asp Leu Cys Val Ala Asn Thr
                20                  25                  30

Leu Phe Ala Leu Asn Leu Phe Lys His Leu Ala Lys Ala Ser Pro Thr
            35                  40                  45

Gln Asn Leu Phe Leu Ser Pro Trp Ser Ile Ser Ser Thr Met Ala Met
        50                  55                  60

Val Tyr Met Gly Ser Arg Gly Ser Thr Glu Asp Gln Met Ala Lys Val
65                  70                  75                  80

Leu Gln Phe Asn Glu Val Gly Ala Asn Ala Val Thr Pro Met Thr Pro
                85                  90                  95

Glu Asn Phe Thr Ser Cys Gly Phe Met Gln Gln Ile Gln Lys Gly Ser
                100                 105                 110

Tyr Pro Asp Ala Ile Leu Gln Ala Gln Ala Ala Asp Lys Ile His Ser
            115                 120                 125

Ser Phe Arg Ser Leu Ser Ser Ala Ile Asn Ala Ser Thr Gly Asn Tyr
        130                 135                 140

Leu Leu Glu Ser Val Asn Lys Leu Phe Gly Glu Lys Ser Ala Ser Phe
145                 150                 155                 160

Arg Glu Glu Tyr Ile Arg Leu Cys Gln Lys Tyr Tyr Ser Ser Glu Pro
```

```
                       165                           170                           175
 Gln Ala Val Asp Phe Leu Glu Cys Ala Glu Glu Ala Arg Lys Lys Ile
             180                     185                     190

Asn Ser Trp Val Lys Thr Gln Thr Lys Gly Lys Ile Pro Asn Leu Leu
         195                     200                 205

Pro Glu Gly Ser Val Asp Gly Asp Thr Arg Met Val Leu Val Asn Ala
     210                     215                 220

Val Tyr Phe Lys Gly Lys Trp Lys Thr Pro Phe Glu Lys Lys Leu Asn
 225                     230                 235                 240

Gly Leu Tyr Pro Phe Arg Val Asn Ser Ala Gln Arg Thr Pro Val Gln
             245                     250                 255

Met Met Tyr Leu Arg Glu Lys Leu Asn Ile Gly Tyr Ile Glu Asp Leu
             260                     265                 270

Lys Ala Gln Ile Leu Glu Leu Pro Tyr Ala Gly Asp Val Ser Met Phe
         275                     280                 285

Leu Leu Leu Pro Asp Glu Ile Ala Asp Val Ser Thr Gly Leu Glu Leu
     290                     295                 300

Leu Glu Ser Glu Ile Thr Tyr Asp Lys Leu Asn Lys Trp Thr Ser Lys
 305                     310                 315                 320

Asp Lys Met Ala Glu Asp Glu Val Glu Val Tyr Ile Pro Gln Phe Lys
                 325                     330                 335

Leu Glu Glu His Tyr Glu Leu Arg Ser Ile Leu Arg Ser Met Gly Met
             340                     345                 350

Glu Asp Ala Phe Asn Lys Gly Arg Ala Asn Phe Ser Gly Met Ser Glu
         355                     360                 365

Arg Asn Asp Leu Phe Leu Ser Glu Val Phe His Gln Ala Met Val Asp
     370                     375                 380

Val Asn Glu Glu Gly Thr Glu Ala Ala Ala Gly Thr Gly Gly Val Met
 385                     390                 395                 400

Thr Gly Arg Thr Gly His Gly Gly Pro Gln Phe Val Ala Asp His Pro
                 405                     410                 415

Phe Leu Phe Leu Ile Met His Lys Ile Thr Asn Cys Ile Leu Phe Phe
             420                     425                 430

Gly Arg Phe Ser Ser Pro
             435
```

POLYNUCLEOTIDE CONSTRUCTS FOR SECRETED GLYCOSYLATED PLASMINOGEN ACTIVATOR INHIBITOR-2 (PAI-2)

TECHNICAL FIELD

The invention relates to enhanced secretion of PAI-2, to recombinant polynucleotide constructs suitable for providing enhanced secretion of PAI-2, to the expression products of those constructs and to their uses, as well as a 414 amino acid form of PAI-2, a synthetic signal peptide used in the preparation of glycosylated, secreted PAI-2 and 60 kD glycosylated, secreted, recombinant PAI-2.

DEPOSITION OF MICROORGANISMS

BTA 1445, an *E. coli* strain harbouring a PAI-2 encoding construct was deposited with the American Type Culture Collection of 12301 Parklawn Drive, Rockville, Md. 20852 U.S.A. under the provisions of the Budapest Treaty on 11 Feb. 1987 under accession number ATCC 53585.

BACKGROUND ART

Plasminogen activator (PA) inhibitor Type 2 (PAI-2) is one of four immunologically distinct groups of PA inhibitors. PA inhibitors are members of the serpin gene family.

PAI-2, also termed minactivin, has been purified from the human monocytic cell line U937 (International Patent Application PCT/AU85/00191 published as WO86/01212 and PCT/AU87/00068 published as WO87/05628). It has also been detected in pregnancy plasma and in the conditioned medium of several human cells including peripheral blood monocutes, HT1080 fibrosarcoma cells and HEp3 laryngeal carcinoma cells.

Distinct molecular weight species of PAI-2 have been identified:

A 46 kD form is non-glycosylated and primarily cell associated. This form has been found in lysates of U937 cells and purified from the conditioned medium of phorbol ester (PMA) stimulated U937 cells (International Patent Application No. PCT/AU87/00068).

A 60 kD glycosylated form has been found to be secreted by U937 cells (Genton et al., 1987) as well as being present in the maternal plasma of pregnant women (Lecander and Astedt, 1986).

The non-glycosylated 46kD intracellular form accounts for 80-90% of PAI-2 synthesized in U937 (Genton et al., 1987) and HT1080 cells (Medcalf et al., 1988)

Examination of the primary amino acid sequence of PAI-2 reveals that the molecule lacks the characteristic transient signal peptide usually found at the amino (NH$_2$)-terminus of secreted proteins. Although the NH$_2$- terminus of the purified 46 kD form of PAI-2 from U937 cells has not been determined, apparently because it is blocked (Kruithof et al, 1986), the NH$_2$-terminus of the 60 kD glycosylated version has been reported to be the initiator methionine (residue 1, Ye et al., 1988). This implies that secretion occurs without cleavage of a signal peptide from PAI-2. The mode of translocation of PAI-2 through the cell is not understood, however an internal signal has been proposed (Ye et al., 1988).

As is the case with most potent biologically active proteins, PAI-2 is produced in very small amounts in vivo and as such is difficult to purify and characterise by conventional biochemical approaches. The recent cloning of the gene for PAI-2 and its expression in bacterial cells (International Patent Application No. PCT/AU87/00068) now allows the production of significant quantities of purifed 46 kD PAI-2 which is needed to evaluate its biological efficacy in clinical applications. However this bacterial material is not glycosylated, nor modified post-translationally in a manner analogous to that secreted by human cells. Therefore it is desirable to produce glycosylated forms of PAI-2 using transfected mammalian cells, since the two forms of PAI-2 may differ in their biological activities e.g. binding affinity for urokinase, PA specificity, immunogenicity, in vivo half-life etc.

The native PAI-2 gene has previously been expressed in a number of heterologous mammalian expression systems (International Patent Application No. PCT/AU87/00068). Although PAI-2 is synthesized in these systems, expression levels are low, and the majority of the product (approx. 90%) is non-glycosylated and intracellular. PAI-2 produced in this form is a suitable molecule for prophylactic, therapeutic and/or diagnostic uses but its use is limited by the quantities obtainable and limited glycosylation. It is still desirable to be able to attain efficient secretion, of the 60 kD glycosylated molecule, in order to be able to use the molecule for prophylactic, therapeutic and/or diagnostic purposes on a clinical scale.

In addition to expression of PAI-2 in mammalian cells (International Patent Application No. PCT/AU87/00068), workers have attempted to secrete the 60 kD form of PAI-2. A Swedish group has attempted to secrete PAI-2 from transfected CHO cells but could not detect any secretion of 60 kD PAI-2 (Ny et al, 1988, Ny et al, 1989). A Swiss group attempted the secretion of PAI-2 using transfected WISH cells but likewise found that most of the PAI-2 material was of the intracellular form. Although some high molecular weight material was found in the culture medium, it was not demonstrated that the material was glycosylated (Belin, D., Wohlwend, A., and Vassalli, J. D. (1989); Belin, D., Wohlwend, A., Schleuning, W-D, Kruithof, E. K. O. and Vassalli, J. D. (1989)). The material may have been partially glycosylated because the mobility was different from U937 high molecular weight PAI-2.

Previous studies have shown that the addition of a heterologous hydrophobic signal domain to the NH$_2$-terminus of a cytoplasmic protein may result in certain circumstances in the translocation of the cytoplasmic protein across the endoplasmic reticulum (Hiebert and Lamb, 1988). Translocation across the ER is the first step along the secretory pathway. The nature of the heterologous signal peptide (e.g. whether or not it is cleaved from the protein) and the inherent properties of the cytoplasmic protein (e.g. the presence of other transport or membrane retention signals) then determine whether the chimeric protein is secreted, anchored to a cellular membrane or degraded.

Because of the complexity of the secretion mechanisms it is not possible to convert in a predictable manner a cytoplasmic non-glycosylated molecule into a secreted, glycosylated molecule. Even if by the addition of a signal sequence a cytoplasmic molecule is secreted, the processing (i.e. cleavage) of the added signal sequence may occur at different unpredictable locations.

Transient NH$_2$- terminal signal sequences found on most secreted proteins are identified by three distinct regions—a basic N-terminal region which may contain charged residues, a central hydrophobic core and a C-terminal region containing the signal peptidase recognition site.

There is no consensus sequence for signal peptidase recognition although von Heijne (1986) has developed rules that take account of many of the known cleavage sites. The application of these rules, however, does not necessarily allow the prediction of cleavage sites when they are applied to cytoplasmic molecules bearing heterologous signal sequences.

DISCLOSURE OF THE INVENTION

In accordance with the present invention, the addition of selected or designed signal sequences to PAI-2 not only facilitates secretion of the glycosylated 60 kD form of PAI-2 but also directs correct processing of the signal. In addition, by utilising these signal sequences, PAI-2 has been secreted either with or without its N-terminal methionine residue.

DEFINITIONS

As used throughout the specification the expressions "PAI-2 variant" and "variant of PAI-2" refer to a molecule derived from PAI-2 by alteration to the $NH_2$-terminus thereof to provide an efficient signal sequence for secretion of the glycosylated molecule from a host cell.

The term "parenteral" as used herein includes subcutaneous injections, intravenous, or intramuscular injection, or infusion techniques.

The term "synthetic signal peptide" as used throughout the specification refers to a peptide which is made in vitro or in vivo by translating a synthesized oligo-deoxyribonucleotide sequence.

According to a first embodiment of this invention there is provided a process for the preparation of recombinant, glycosylated, secreted PAI-2 or recombinant glycosylated secreted PAI-2 without its N-terminal methionine, which process comprises:

providing a construct comprising a first polynucleotide molecule encoding PAI-2 or PAI-2 without its N-terminal methionine; and attaching a polynucleotide molecule encoding a transient signal sequence to the 5' end of the first polynucleotide molecule, such that the resulting hybrid protein expressed from the construct will consist of a transient signal sequence attached to the $NH_2$- terminal of PAI-2 or of PAI-2 without its N-terminal methionine; and expressing the construct in a eukaryotic host cell.

The signal peptide may be attached to the N-terminal methionine of PAI-2 or alternatively the N-terminal methionine may be deleted, and the signal peptide attached to the next residue, viz glutamic acid.

The signal peptide is designed to be cleaved during translocation of the PAI-2 molecule across the endoplasmic reticulum of the host cell.

The signal peptide may be a synthetic signal peptide.

Generally, the synthetic signal sequence is designed so that it has three distinct regions—a basic N-terminal region which may contain charged residues, a central hydrophobic core and a C-terminal region containing the signal peptidase recognition site. Attempts at designing signal peptidase cleavage sites can be assisted using the method of von Heijne (1986).

A preferred synthetic peptide is:
  MKCLLLALGLLAFUPLVRA (SEQ ID NO: 1)

The signal peptide may be naturally occurring.

A preferred natural signal peptide is the signal peptide from the protein human α-1-antitrypsin:
  MPSSVSWGILLLAGLCCLVPVSLA (SEQ ID NO: 2)

Other natural signal peptides could function in an analagous manner to the α-1-antitrypsin signal when fused to the $NH_2$-terminus of PAI-2.

According to a second embodiment of the invention there is provided a recombinant glycosylated PAI-2 encoding construct comprising a polynucleotide molecule encoding a transient signal peptide attached to the $NH_2$-terminal methionine or the $NH_2$- terminal glutamic acid of PAI-2.

Preferably, the construct is a DNA molecule.

According to a third embodiment of the invention there is provided a variant of PAI-2 comprising an altered $NH_2$-terminus wherein the $NH_2$-terminus of PAI-2 is altered to provide an efficient signal peptide.

Typically, the alteration is in the first 22 amino acids of the amino acid sequence of PAI-2.

Preferably, all or some of the asparagine residues at positions 8 and 14, lysine at position 17, and the histidine at position 18 are replaced. Preferably replacement is by in vitro mutagenesis. Preferably the amino acids are replaced by a more hydrophobic amino acid selected from Leu, Phe, Ala, Met, Thr, Ser, Ile and Val.

According to a fourth embodiment of this invention there is provided a polynucleotide molecule encoding a PAI-2 variant of the third embodiment. Preferably, the polynucleotide molecule is a DNA molecule.

According to a fifth embodiment of this invention there is provided the synthetic peptide:
  MKCLLLALGLLAFVPLVRA (SEQ ID NO: 3)

Preferably, the signal encoding sequences are prepared by DNA synthesis regardless of whether they are synthetic or naturally occurring signal sequences.

According to a sixth embodiment of the invention there is provided a recombinant DNA molecule comprising a polynucleotide molecule of the second embodiment or of the fourth embodiment which polynucleotide molecule is a DNA molecule, and vector DNA.

Typically, the vector DNA is plasmid DNA.

Preferred plasmid vectors of the invention include pGEM4Z, PSVL, pBTA613, pBTA830 and baculovirus transfer vectors such as pAC373.

Preferred recombinant DNA molecules of the invention include pBTA822, pBTA823, pBTA825, pBTA826, pBTA827, pBTA828 and pBTA839.

According to a seventh embodiment of the invention there is provided a transformed host cell transformed by a recombinant DNA molecule of the sixth embodiment.

Typical host cell lines are derived from eukaryotic organisms and include monkey kidney COS cells, the monkey kidney cell line Vero, Chinese Hamster Ovary (CHO) cells, the human histiocytic lymphoma U937 cell line, derivatives of CHO-KL cells, for example DG44, the hamster kidney cell line BHK-21, the human kidney cell line 293, the human epithelial cell derived line HeLa S3 and the human monocute cell line HL60 and cell lines derived from the insects Spodoptera frugiperda and Bombyx mori.

Preferably, the transformation is carried out by the calcium phosphate method or by electroporation.

According to an eighth embodiment of this invention there is provided an expression product of a transformed host cell of the seventh embodiment. The expression product is glycosylated PAI-2 or a variant of PAI-2.

The invention also provides the 414 amino acid form of PAI-2 which lacks the N-terminal methionine of native PAI-2 in glycosylated and unglycosylated form. In addition the invention provides for the first time recombinant, glycosylated, secreted 60 kD PAI-2.

According to a ninth embodiment of this invention there is provided a composition comprising an effective amount of an expression product of the eighth embodiment, or of the 60 kD glycosylated, secreted recombinant PAI-2, or of the 414 amino acid form of PAI-2 together with a pharmaceutically acceptable carrier, diluent, excipient, and/or adjuvant.

According to a tenth embodiment of this invention there is provided a process for preparing a recombinant DNA molecule of the sixth embodiment which process comprises inserting a DNA molecule of the second embodiment or of the fourth embodiment into vector DNA.

According to an eleventh embodiment of this invention there is provided a process for preparing a transformed host cell of the seventh embodiment which process comprises making a host cell competent for transformation and transforming said competent host cell with a recombinant DNA molecule of the sixth embodiment.

According to a twelfth embodiment of this invention there is provided a process for preparing an expression product of the eighth embodiment which process comprises culturing a transformed host cell of the seventh embodiment and separating the expression product from the culture.

According to a thirteenth embodiment of this invention there is provided a process for preparing a composition of the ninth embodiment which process comprises admixing an expression product of the eighth embodiment or 60 kD recombinant glycosylated secreted PAI-2, or the 414 amino acid form of PAI-2 with a pharmaceutically acceptable carrier, diluent, excipient, and/or adjuvant.

According to a fourteenth embodiment of this invention there is provided an antibody raised against an expression product of the eighth embodiment or against recombinant secreted glycosylated 60 kD PAI-2, or against the 414 amino acid form of PAI-2, or against a composition of the ninth embodiment.

According to a fifteenth embodiment of this invention there is provided an antibody composition comprising an effective amount of an antibody of the fourteenth embodiment together with a pharmaceutically acceptable carrier, diluent, excipient, and/or adjuvant.

According to a sixteenth embodiment of this invention there is provided a method of passively vaccinating a host in need of such treatment which method comprises administering an effective amount of an antibody of the fourteenth embodiment or an antibody composition of the fifteenth embodiment, to the host.

According to a seventeenth embodiment of this invention there is provided a process for producing an antibody of the fourteenth embodiment which process comprises immunising an immunoresponsive host with an expression product of the eighth embodiment, or recombinant glycosylated secreted 60 kD PAI-2, or the 414 amino acid form of PAI-2, or a composition of the ninth embodiment.

According to a eighteenth embodiment of the invention there is provided an expression product of the eighth embodiment produced by the process of the twelfth embodiment.

According to a nineteenth embodiment there is provided an antibody of the fourteenth embodiment produced by the process of the seventeenth embodiment.

The antibodies produced may be monoclonal or polyclonal antibodies. For the production of monoclonal antibodies the PAI-2 molecules of the invention are used as immunogens according to standard techniques for the preparation of monoclonal antibodies.

According to a twentieth embodiment of the invention there is provided a diagnostic kit containing an expression product, and/or composition, and/or antibody and/or antibody composition, respectively of the eighth, ninth, fourteenth and fifteenth embodiments, and/or the 414 amino acid form of PAI-2 and/or 60 kD glycosylated secreted recombinant PAI-2, together with positive and negative standards as controls.

According to a twenty-first embodiment of this invention there is provided a reagent for locating and defining the boundaries of tumours in histological specimens or in vivo which reagent comprises a suitably labelled expression product of the eighth embodiment, or suitably labelled 60 kD recombinant secreted glycosylated PAI-2, or suitably labelled 414 amino acid form of PAI-2.

According to a twenty-second embodiment of this invention there is provided a method of locating and defining the boundaries of tumours in histological specimens or in vivo which method comprises applying or administering a reagent according to the twenty-first embodiment to the specimen or patient respectively and subsequently imaging to determine the site of the concentration of the label.

According to a twenty-third embodiment of this invention there is provided a method of inhibiting tumour invasion or treating tumours comprising administering to a patient requiring such treatment a therapeutically effective amount of an expression product of the eighth embodiment or a composition of the ninth embodiment or 60 kD glycosylated secreted recombinant PAI-2 or the 414 amino acid form of PAI-2 either labelled or unlabelled.

According to a twenty-fourth embodiment of this invention there is provided a method of treatment of chronic inflammation such as rheumatoid arthritis comprising administering to a patient requiring such treatment a therapeutically effective amount of an expression product of the eighth embodiment or a composition of the ninth embodiment or recombinant glycosylated secreted 60 kD PAI-2 or the 414 amino acid form of PAI-2 either labelled or unlabelled.

Labels to be used in conjunction with 60 kD PAI-2, expression products and 414 amino acid forms of PAI-2 in accordance with this invention are those standardly used in the art for labelling for the purposes of diagnosis, in vitro detection, imaging, or therapy.

According to a twenty-fifth embodiment of this invention there is provided a method of monitoring chronic inflammation comprising the detection of PAI-2 in samples of body fluids and tissues using antibodies of the fourteenth embodiment or an antibody composition of the fifteenth embodiment.

According to a twenty-sixth embodiment of the invention there is provided a method of monitoring chronic inflammation comprising using an expression product of the eighth embodiment, recombinant glycosylated secreted 60 kD PAI-2 or the 414 amino acid form of PAI-2.

The PAI-2 variants expression products, 414 amino acid form of PAI-2 and recombinant glycosylated secreted 60 kD PAI-2 produced in accordance with this invention are of use in the following areas:

therapy, prophylaxis and diagnosis of inflammatory disease;

therapy, prophylaxis and diagnosis of cancer metastasis and proliferation;

therapy of transplant and placenta rejection crises and graft-versus-host reactions;

therapy and diagnosis of autoimmune diseases and diseases associated with excessive oxygen radical production;

therapy and prophylaxis of wound and bone healing disorders, tissue damage during or after acute reperfusion, and subarahnoidal bleeding disorders;

as topical medicaments for promoting fibrin adhesion, promoting healing of wounds and burns;

treating asthma and treating or preventing diseases associated with high leukocyte activity; and suppression of the monocute-macrophage system.

Specific examples from the above classes of disease include:

rheumatoid arthritis
osteoarthritis
colitis ulcerosa
systemic lupus erythematosus
multiple sclerosis
psoriasis
pemphigus
corneal and duodenal ulceration
purpura
periodontitis
muscular dystrophy The amount of expression product, 60 kD glycosylated secreted recombinant PAI-2 or 414 amino acid form of PAI-2 that may be combined with carrier to produce a single dosage form will vary depending upon the condition being treated, the host to be treated and the particular mode of administration.

It will be understood, also, that the specific dose level for any particular patient will depend upon a variety of factors including the activity of the specific protein product or antibody employed, the age, body weight, general health, sex, diet, time of administration, route of administration, rate of excretion, drug combination, the particular state being treated and the severity of the particular condition undergoing treatment.

The compositions of the present invention may be administered parenterally or topically or potentially via mucosal routes in dosage unit formulations containing conventional, non-toxic, pharmaceutically acceptable carriers, diluents, adjuvants and/or excipients as desired.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including sythetic mono- or diglycerides, In addition, fatty acids such as oleic acid find use in the preparation of injectables.

The term "pharmaceutically acceptable adjuvant" can mean either the standard compositions which are suitable for human administration or the typical adjuvants employed in animal vaccinations.

At present alum is the only registered adjuvant for human use however, experimental work is being conducted on other adjuvants for human use and it is anticipated that these other adjuvants would be suitable for use in preparing compositions for human vaccination in accordance with this invention.

Suitable adjuvants for the vaccination of animals include but are not limited to oil emulsions such as Freund's complete or incomplete adjuvant (not suitable for livestock use), Marcol 52: Montanide 888 (Marcol is a Trademark of Esso. Montanide is a Trademark of SEPPIC, Paris), squalane or squalene, Adjuvant 65 (containing peanut oil, mannide monooleate and aluminium monostearate), mineral gels such as aluminium hydroxide, aluminium phosphate, calcium phosphate and alum, surfactants such as hexadecylamine, octadecylamine, lysolecithin, dimethyldioctadecylammonium bromide, N,N-dioctadecyl-N',N'-bis(2-hydroxyethyl) propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. The expression products of the present invention can also be administered following incorporation into liposomes or other micro-carriers, or after conjugation to polysaccharides, proteins or polymers or in combination with Quil-A to form "Iscoms" (Immunostimulating complexes) (Morein et al., Nature 308, 457–460[19841). Other adjuvants suitable for use in the present invention include conjugates comprising the expression product together with an integral membrane protein of prokaryotic origin, such as TraT. (See PCT/AU87/00107)

Routes of administration, dosages to be administered as well as frequency of injections are all factors which can be optimized using ordinary skill in the art. Typically, the initial vaccination is followed some weeks later by one or more "booster" vaccinations, the net effect of which is the production of high titres of antibodies against the immunogen.

Compositions for topical administration include creams, ointments and pastes. The ingredients that constitute the base of ointments (e.g. petrolatum, waxes) are melted together, powdered drug components are added and the mass stirred with cooling. Generally, the product is then passed through a roller mill to achieve the particle-size range desired for the dispersed solid. Pastes are ointments with relatively large, dispersed solid content, and are prepared similarly.

Creams are semisolid emulsions, either water-in-oil or oil-in-water. A solid ingredient can be added to the appropriate phase before emulsification or may be dispersed at some point after the emulsification step. Topical dosage forms include disc dosage form systems that have been used for transdermal delivery of therapeutic agents. They provide uniform and prolonged drug release.

It would be desirable in patients suffering from particular disease states to be able to administer the compositions of the invention either orally, rectally or possibly even vaginally. Compositions which could be used in these ways could be prepared as follows:

Suppositories for rectal or vaginal administration of the compositions of the invention can be prepared by mixing the composition with a suitable nonirritating exipient such as cocoa butter, theobroma oil, glycerinated gelatin or polyethylene glycols which are solid at ordinary temperatures but liquid at rectal or vaginal temperature or by contact with fluids present in the appropriate cavity and will therefore melt in the rectum or vagina and release the drug.

Solid dosage forms for oral administration may include capsules, tablets, pills, powders, and granules. In such solid dosage forms, expression products, recombinant glycosylated secreted 60 kD PAI-2 or 414 amino acid form of PAI-2 may be admixed with at least one inert diluent such as sucrose, lactose starch or hydrolysed gelatin. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include nanoparticles, microcapsules, LTB conjugates, cholera or its B subunit as a conjugate, or vitamin B12 conjugates in pharmaceutically acceptable emulsions, syrups, solutions, suspensions, and elixirs containing inert diluents commonly used in the art, such as water. Such compositions may also comprise adjuvants, such as wetting agents, emulsifying and suspending agents or TraT as a conjugate, and sweetening, flavouring, and perfuming agents including sugars such as sucrose, sorbitol, fructose etc, glycols such as polyethylene glycol, propylene glycol etc, oils such as sesame oil, olive oil, soybean oil etc, antiseptics such as alkylparahydroxybenzoate etc, and flavours such as strawberry flavour, peppermint etc.

The recombinant constructs of the invention provide expression of secreted and glycosylated forms of PAI-2.

BRIEF DESCRIPTION OF DRAWINGS

FIG. 1 (SEQ ID NOS 5-13) shows the sequence of oligonucleotides and encoded signal peptides employed in construction of the in vitro and in vivo PAI-2 expression vectors.

FIG. 6 shows urokinase binding to PAI-2 secreted from transfected COS cells immunoprecipitated with anti-PAI-2 antibodies and electrophoresed through an SDS-PAG.

FIG. 7 (SEQ ID NOS 14 and 15) shows DNA and amino acid sequence of preA-PAI2 VIZ PAI-2 plus synthetic signal. Amino acids in capitals indicate the signal sequence.

FIG. 8 (SEQ ID NOS 10 AND 17) shows DNA and amino acid sequence of preB-PAI-2 VIZ PAI-2 plus α-1-antitrypsin signal. Amino acids in capitals indicate the signal sequence.

FIG. 11 shows the secretion of 60,000 Mr PAI-2 into the medium from a CHO-K1 cell line stably transfected with pBTA 827. The PAI-2 was immunoprecipitated from the medium and then fractionated by SDS-PAGE.

BEST MODE FOR CARRYING OUT THE INVENTION

Figure 2A:
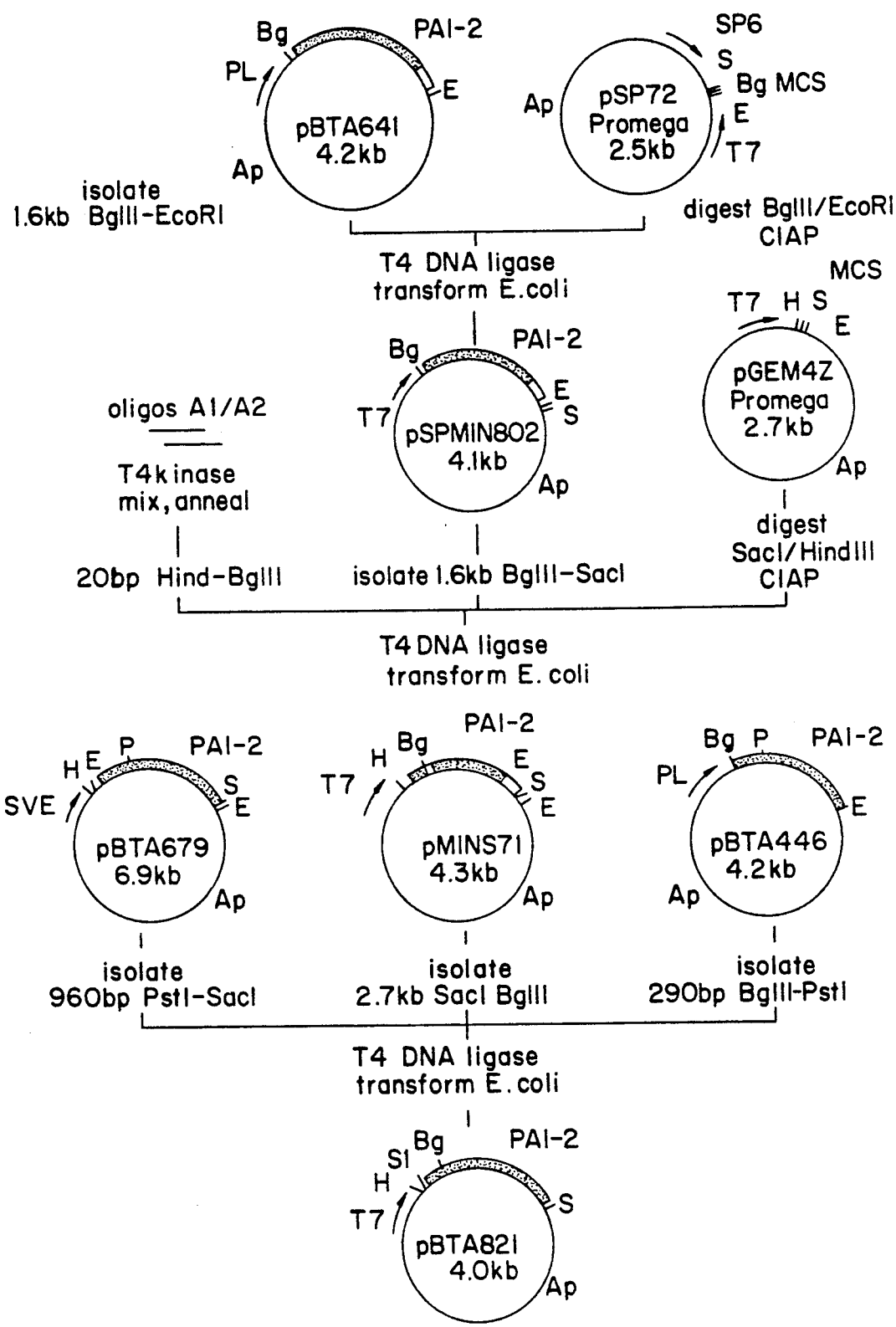
FIG. 2A–C shows construction of in vitro expression vectors:
  A: PBTA 821 containing PAI-2 gene without signal
  B: PBTA 822 containing PAI-2 gene with synthetic signal
  C: PBTA 823 containing PAI-2 gene with α-1-antitrypsin signal

The recombinant DNA molecules and transformed host cells of the invention are prepared using standard techniques of molecular biology.

Expression products of the invention are obtained by culturing the transformed host cells of the invention under standard conditions as appropriate to the particular host cell and separating the expression product from the culture by standard techniques. The expression product may be used in impure form or may be purified by standard techniques as appropriate to the expression product being produced.

The compositions of the invention are prepared by mixing, preferably homogeneously mixing, expression product, 60 kD recombinant secreted glycosylated PAI-2 or the 414 amino acid form of PAI-2 with a pharmaceutically acceptable carrier, diluent, excipient and/or adjuvant using standard methods of pharmaceutical preparation.

The amount of expression product, recombinant glycosylated secreted 60 kD PAI-2, or the 414 amino acid form of PAI-2 required to produce a single dosage form will vary depending upon the condition to be treated, patient to be treated and the particular mode of administration. The specific dose level for any particular patient will depend upon a variety of factors including the activity of the expression product or PAI-2 molecule employed, the age, body weight, general health, sex, and diet of the patient, time of administration, route of administration, rate of excretion, drug combination and the severity of the condition undergoing treatment.

The composition may be administered parenterally or topically, or possibly by inhalation spray, vaginally, orally or rectally in unit dosage formulations containing conventional, non-toxic, pharmaceutically acceptable carriers, diluents, excipients and/or adjuvants as desired.

Antibodies are raised using standard vaccination regimes in appropriate hosts. The host is vaccinated with an expression product, recombinant glycosylated secreted 60 kD PAI-2 or the 414 amino acid form of PAI-2 or a composition of the invention.

The antibody composition is prepared by mixing, preferably homogeneously mixing, antibody with a pharmaceutically acceptable carrier, diluent, excipient and/or adjuvant using standard methods of pharmaceutical preparation.

The amount of antibody required to produce a single dosage form will vary depending upon the condition to be treated, patient to be treated and the particular mode of administration. The specific dose level for any particular patient will depend upon a variety of factors including the activity of the antibody employed, the age, body weight, general health, sex, and diet of the patient, time of administration, route of administration, rate of excretion, drug combination, and severity of the condition undergoing treatment.

The antibody composition may be administered parenterally in unit dosage formulations containing conventional, non-toxic, pharmaceutically acceptable carriers, diluents, excipients and/or adjuvants as desired.

Diagnostic kits are prepared by formulating expression product and/or antibodies and/or recombinant glycosylated secreted 60 kD PAI-2 and/or the 414 amino acid form of PAI-2 at appropriate concentration to the substance(s) to be detected with a pharmaceutically acceptable carrier, diluent, excipient and/or adjuvant. A positive control standard of a known concentration of the substance to be detected is prepared similarly. The negative standard comprises carrier, diluent, excipient and/or adjuvant alone. Examples of diagnostic kits include a tumour diagnostic wherein the reagent comprises anti-expression product antibodies and the positive control comprises an expression product standard of known concentration.

We have constructed two variants of PAI-2 that are efficiently secreted from mammalian cells; both contain an NH$_2$-terminal signal designed to be cleaved during translocation across the endoplasmic reticulum (ER). One of these signals is an artificial signal that we designed according to the above description of signal peptides. It has the sequence: (SEQ ID NO: 1)

M K C L L L A L G L L A F V P L V R A

The second signal is the natural signal peptide from the protein human α-1-antitrypsin: (SEQ ID NO: 2)

M P S S V S W G I L L L A G L C C L V P V S L A.

However it is possible that other natural signal peptides could function in an analogous manner to the α-1-antitrypsin signal when fused to the NH$_2$- terminus of PAI-2. The examples of signal peptides described are by way of example only and are not intended to be limiting on the scope of the invention.

The first PAI-2 signal-containing variant was constructed such that the artificial signal was fused to the NH$_2$-terminal methionine of PAI-2. Correct cellular processing of this signal peptide should result in a mature PAI-2 molecule of 415 amino acids with Met at its NH$_2$-terminus. The second variant of PAI-2 was constructed by fusing the human α-1-antitrypsin signal peptide to PAI-2 without is NH$_2$-terminal methionine. After correct cellular processing a mature PAI-2 molecule of 414 residues having a glutamic acid residue at its NH$_2$-terminus should be generated. Details of the construction of the signal-PAI-2 molecules and their expression in both in vitro and in vivo systems are described below.

An alternative to adding heterologous signal peptides to PAI-2 in order to have PAI-2 secreted efficiently from mammalian cells could be to modify the native PAI-2 sequence. The first 22 amino acids of PAI-2 contain a stretch of hydrophobic residues characteristic of a signal peptide. However experiments below show that this region does not behave as a typical signal i.e. it does not promote translocation of PAI-2 across the ER. However, since some high molecular weight glycosylated PAI-2 has been found in culture media and plasma, residues 1-22 may represent an inefficient signal. The hydrophobic nature of the NH$_2$- terminal 22 residues of PAI-2 is compromised by 2 asparagine residues (positions 8 and 14), a lysine at position 17, and a histidine at 18. In vitro mutagenesis of this region to replace one or more of these residues with a more hydrophobic amino acid (e.g. Leu, Phe, Ala, Met, Thr, Ser, Ile, Val) could improve the efficiency with which this region acts as a signal peptide. A signal peptidase recognition site is predicted after Ala$_{22}$. Thus these PAI-2 variants may be secreted without their first 22 residues. Although this region is conserved between members of the serpin gene family its presence may not be required for biological activity of PAI-2.

CONSTRUCTION OF VECTORS FOR EXPRESSION OF SIGNAL-PAI-2 VARIANTS

For details of recombinant DNA techniques used see Maniatis et al (1982). Oligonucleotides encoding the signal peptides (FIG. 1) were synthesized on an Applied Biosystems DNA synthesizer (Model 380A), and purified through a polyacrylamide gel. Complementary oligonuclotides (A1 and A2 or B1 and B2 or C1 and C2) were mixed in a 1:1 molar ratio and phosphorylated with 5 units T4 polynucleotide kinase in 65mM Tris-Cl pH 7.5, 10mm MgCl$_2$, 5 mM dithiothreitol, 1 mM ATP. The mixture was heated to 100° C. for 3 minutes and cooled slowly to room temperature to allow annealing to take place.

The annealed signal peptide oligonucleotides were ligated to the PAI-2 coding sequences and cloned into the vectors pGEM4Z (Promega), PSVL (Pharmacia) pBTA613 and pBTA830. The first vector, pGEM4Z, is useful for expressing gene products in a cell-free transcription/translation system; PSVL is useful for transient expression in monkey kidney COS cells; pBTA613 and pBTA830 are vectors that can be selected and stably integrated in mammalian cell lines such as Chinese Hamster Ovary (CHO) cells, Vero, BHK and U937. The signal-PAI-2 gene constructs could also be cloned into any other vector designed for expression in eukaryotic cells.

Figure 2B:
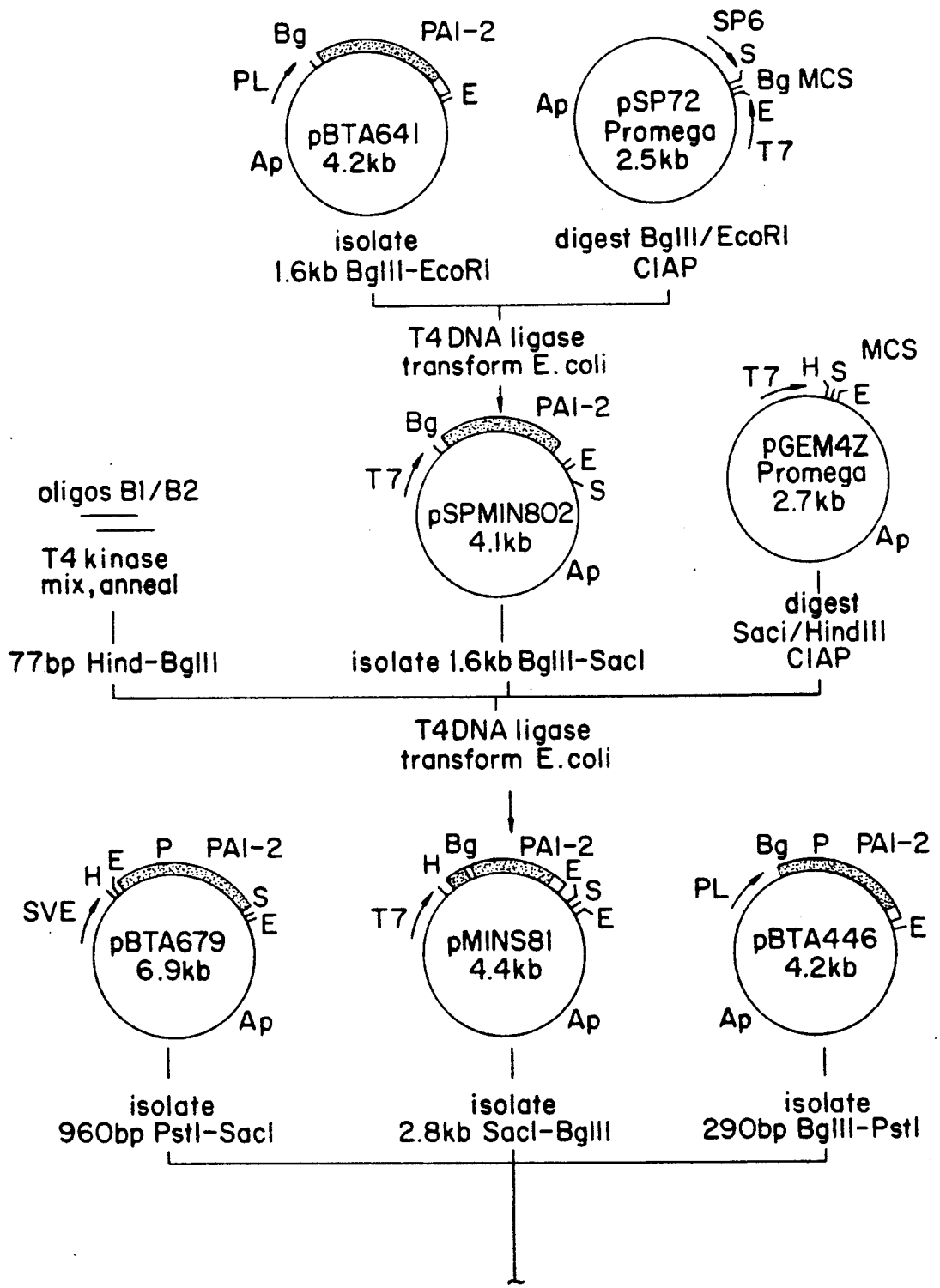
Figure 2C:
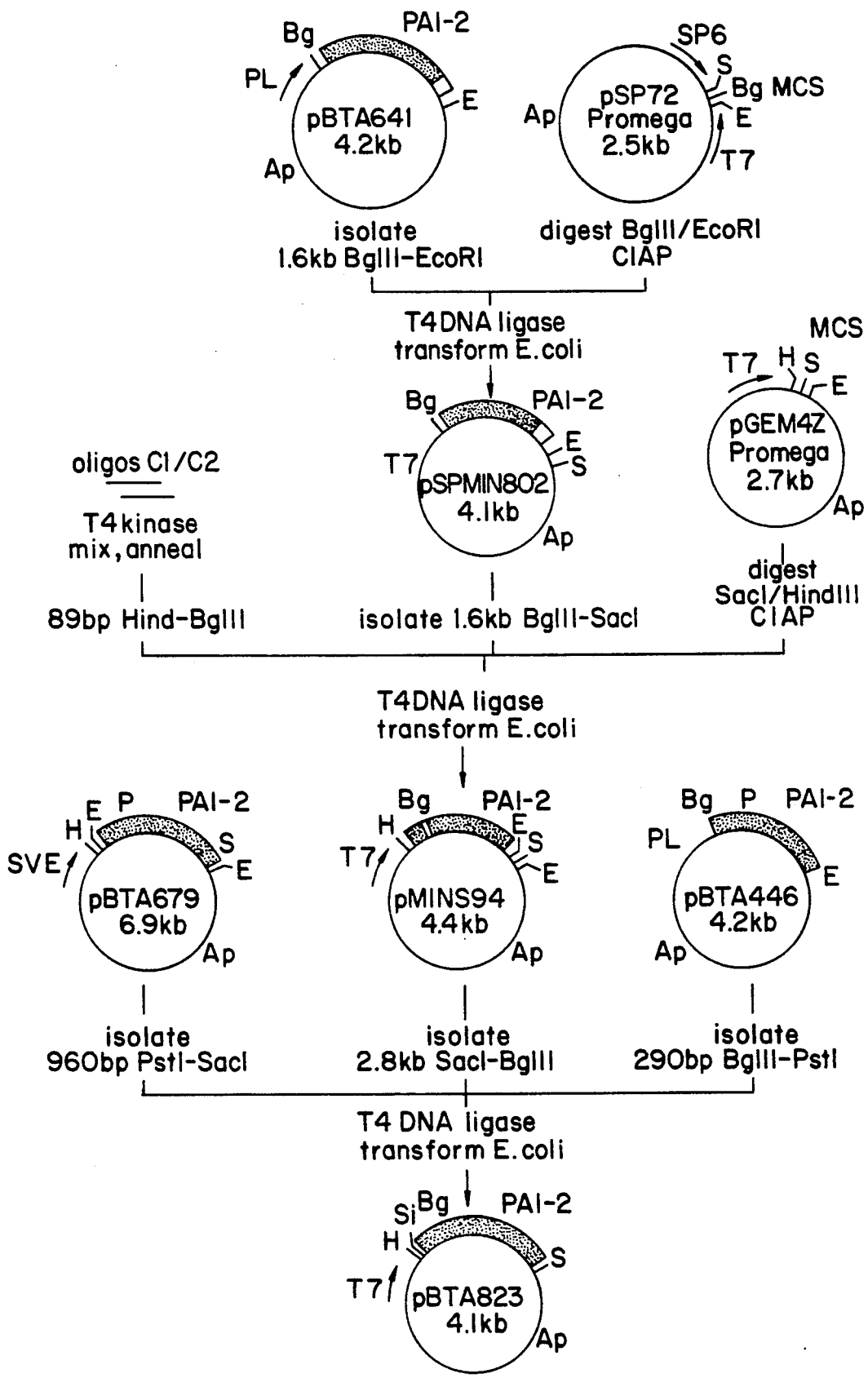

The construction of the recombinant plasmids that express the native PAI-2 gene and the signal PAI-2 variants in an in vitro system and in mammalian cells is illustrated in FIGS. 2 and 3. The various restriction fragments ("inserts" for cloning) were prepared as follows. Restriction enzyme digests of purified plasmid DNA were carried out in buffers recommended by the supplier. Required DNA fragments were separated from the plasmid by gel electrophoresis through 0.8–1.5% Sea-Plaque agarose (FMC Corporation) in Tris-borate buffer (Maniatis et al, 1982). Fragments were visualized by staining with ethidium bromide and UV transillumination. The band of agarose containing the appropriate fragment was sliced out of the gel, melted at 65° C. and the DNA was extracted by passing the diluted material through a NACS column (BRL) as recommended by the supplier. The DNA was then precipitated with ethanol in the presence of carrier TRNA (10 μg/ml).

Vectors were typically prepared as follows. Plasmid DNA purified by CsCl density gradient centrifugation was digested with the appropriate restriction enzymes, the digest was extracted with an equal volume of phenol/chloroform (1:1) and the DNA precipitated with 2.5 volumes of ethanol. The digested DNA was resuspended in 50 mM Tris-Cl pH 9.0, 1 mM MgCl$_2$, 0.1 mM ZnCl$_2$, 1 mm spermidine and incubated with 1–2 units calf intestinal alkaline phosphatase (Boehringer Mannheim) for 30–60 mins at 37° C. The enzyme was heat killed at 70° C. for 15 mins then the DNA was extracted with phenol/chloroform and precipitated with ethanol.

Ligations were carried out as follows. Vector and insert DNAs were mixed at a molar ratio of between 1:1 and 1:5 (1:10 if the insert was smaller than 100 bp) in 1 mM ATP, 10 mM MgCl$_2$, 5 mM DTT, 65 mM Tris-Cl pH 7.5 in a volume of 10–20 μl. Ligations were carried out at 16° overnight with 0.5–1 unit T4 DNA ligase (Boehringer Mannheim). Ligation mixes were diluted to 30 μl with dH$_2$O and 10μl removed for transformation into a competent *E. coli* K12 host (Hanahan, 1985). Transformants were selected by plating onto tryptone-soya agar plates containing 100 μg/ml ampicillin.

Plasmid DNA was extracted from individual colonies (Birnboim and Doly, 1979) and the correct recombinant plasmids identified by restriction analysis. The 5' ends of the PAI-2 gene in pBTA821, 822 and 823 were sequenced to confirm that the signal peptide and methionine start codons were in frame with the remainder of the PAI-2 sequence. Sequencing was carried out on double-stranded plasmid DNA using the Sequenase DNA Sequencing Kit (USB) as described in the instruction manual. The primer used was the T7 primer (Promega).

The plasmids and strains used in the work are summarized in Table 1.

TABLE 1

| BTA Strain # | Plasmid | Host | Description | Signal |
|---|---|---|---|---|
| 1702 | pBTA613[A] | HB101[B] | eukaryotic expression vector | |
| 1737 | pBTA839 | " | 1.3 kb Hind III-EcoRI from pBTA-822 in pBTA 613 | synthetic |
| 1740 | pBTA830[A] | " | eukaryotic expression vector | |
| 1741 | pBTA821 | " | 1.3 kb PAI-2 gene in pGEM4Z[C] | none |
| 1742 | pBTA822 | " | 1.3 kb PAI-2 gene in PGEM4Z | synthetic |
| 1743 | pBTA823 | " | 1.3 kb PAI-2 gene in pGEM4Z | α-1-antitrypsin |
| 1744 | pBTA824 | " | 1.3 kb SalI-SacI from pBTA821 in pSVL[D] | none |
| 1745 | pBTA825 | " | 1.3 kb SalI-SacI from pBTA822 in pSVL | synthetic |

TABLE 1-continued

| BTA Strain # | Plasmid | Host | Description | Signal |
|---|---|---|---|---|
| 1746 | pBTA826 | " | 1.3 kb SalI-SacI from pBTA823 in pSVL | α-1-antitrypsin |
| 1747 | pBTA827 | " | 1.3 kb HindIII-EcoRI from pBTA822 in pBTA830 | synthetic |
| 1748 | pBTA828 | " | 1.3 kb HindIII-EcoRI from pBTA823 in pBTA830 | α-1-antitrypsin |
| 1613 | pBTA446[A] | C600λ[F] | PAI-2 gene in pLK58[E] | none |
| 1650 | pBTA641[A] | N4830[G] | PAI-2 gene in pLK58 | none |
| 1835 | pBTA679[A] | HB101 | PAI-2 gene minus 3' untranslated region derived from pBTA438[E] | none |
| 1445[H] | pBTA438 | JM109[J] | 1.6 kb cDNA coding PAI-2 cloned pUC18 | none |

[A]constructed at Biotechnology Australia Pty Ltd (see text below)
[B]See Maniatis et al 1982
[C]Purchased from Promega
[D]Purchased from Pharmacia LKB Biotechnology
[E]Boterman and Zabeau (1985)
[F]*E. coli* K12 C600λ = thiA1, thr1, leuB6, SupE(gluV)44, lacY1, fhuA21(λ)$^T$
[G]Gottesman et al (1980)
[H]Strain deposited with American Type Culture Collection, of 12301 Parklawn Drive, Rockville MD 20852, USA on 11 February 1987 under accession number ATCC 53585 and described in PCT/AU87/00068
[J]Yanisch-Perron et al (1985)

Plasmid pBTA641 can be derived from pBTA438 as follows. pBTA438 is partially digested with XhoII plus DraI and a 1550 bp fragment isolated and ligated to vector pLK58 cut with BglII and SmaI. The resultant plasmid pBTA446 was linearized with BglII and ligated to a synthetic double stranded 27 mer oligonucleotide having the sequence (SEQ ID NO: 3) GATCT (N)$_{16}$ ATGGAG wherein N represents any nucleotide, containing a bacterial ribosome binding site and the initial nucleotides of the native PAI-2 gene, creating plasmid pBTA641.

pBTA679 contains a 1.3 kb fragment of the PAI-2 gene (including the entire coding region). The 1.3 kb fragment was derived from the 1.6 kb EcoRI-DraI fragment from pBTA438 by deleting 300 bp of 3' untranslated region between the stop codon and the DraI site (at 1604) using Bal 31 nuclease. The resultant fragment with linkers ligated to either end was subcloned into the HindIII-BamHI sites of the multiple cloning site derived from pUC18 (Yanisch-Perron at al, 1985). The end-point of the deletion was determined by sequencing.

pBTA830 is a mammalian cell expression vector. Foreign genes are expressed by cloning into the multiple cloning site (from pUC18) flanked upstream by the SV40 early promoter and downstream by the SV40 small t intron and early polyadenylation signals. pBTA830 comprises the following fragments in order: the 345 bp Pvu.II-HindIII fragment from the SV40 origin (Bethesda Research Laboratories), 51 bp HindIII-EcoRI multiple cloning sites from pUC18, 853 bp XhoI-BamHI fragment from pMSG (a eukaryotic expression vector from Pharmacia) with EcoRI and AatII linkers (GAATTC, GGACGTCC, New England Biolabs) attached to either end, 2262 bp AatII-EagI fragment from pBR327 (Soberon et al, 1980), 345 bp PvuII- HindIII fragment from the SV40 origin, 1320 bp HindIII-SmaI fragment from Tn5 encoding neomycin phosphotransferase (Pharmacia, Beck et al, 1982), 141 bp Sau3A fragment from the SV40 small t intron region, 293 bp Sau3A fragment from the SV40 early polyadenylation region, 288 bp EagI-SalI fragment from pBR327, 345 bp PvuII-HindIII fragment from the SV40 origin, 734 bp HindIII-BglII fragment encoding mouse dihydrofolate reductase from pSV2-DHFR (ATCC 37146, Subramani et al, 1981), 141 bp Sau3A fragment from SV40 small t intron region and 293 bp Sau3A from SV40 early polyadenylation region. Except where indicated incompatible ends were made flush using S1 nuclease or filled in with dNTPs and DNA polymerase I (Klenow).

pBTA613 is a mammalian cell expression vector. Foreign genes are expressed by cloning into the multiple cloning site flanked upstream by the SV40 early promoter and downstream by SV40 polyadenylation signals. pBTA613 comprises the following fragments in order. The 345 bp PvuII-HindIII fragment from the SV40 origin, 51 bp HindIII-EcoRI multiple cloning sites from pUC18, 75 bp EcoRI-AatII fragment from pBR327, 853 bp BamHI-XhoI fragment from PMSG with AatII linkers attached to both ends, 2262 bp AatII-EagI fragment from pBR327, 27 bp oligonucleotide (SEQ ID NO: 4) (GGCCCATATGATATCT-CGAGACTAGTC), 288 bp EagI-SalI fragm pBR327, 345bp PvuII-HindIII fragment from the SV40 origin, 734 bp HindIII-BglII fragment encoding mouse dihydrofolate reductase from pSV2-DHFR, 141 bp Sau3A fragment from SV40 small t intron region and 293 bp Sau3A fragment from SV40 early polyadenylation region. The HindIII site at the 5' end of the dhfr gene was deleted using S1 nuclease, other incompatible ends were made flush using S1 nuclease or filled in with dNTPs and DNA polymerase I (Klenow).

IN VITRO TRANSLATION

In PBTA 821, 822 and 823 the PAI-2 gene is placed downstream from the T7 RNA polymerase promoter. To generate RNA transcripts from the native PAI-2 gene and the signal variants, plasmid DNA purified on CsCl density gradients was linearized then transcribed using the commercially available Riboprobe Gene transcription System (Promega). Where commercially available kits were used experiments were performed according to the manufacturer's instructions.

Typically plasmid DNA was linearized by digestion with EcoRI. The EcoRI digested DNA was treated with proteinase K [at 400 μg/ml] then extracted with phenol/chloroform (1:1), precipitated with 2.5 vols ethanol and resuspended in 10 mm Tris-Cl pH 8.0, 1 mM EDTA. Approximately 1 μg linear DNA was transcribed in a 25 μl reaction containing 1×transcription buffer (Promega), 10 mM DTT, 0.5 mM each ATP, CTP, GTP, UTP, 40 units RNAsin and 7.5 units T7 RNA polymerase (Promega) at 37° for 60 mins.

The RNA transcripts were subsequently translated in a rabbit reticulocyte lysate cocktail. Typically, 1 μl of the transcription reaction (RNA) was added to a cocktail containing 8 μl rabbit reticulocyte lysate (Amersham), 12.5 μCi $^{35}$S-Methionine (SJ1015 Amersham, 1000 Ci/mmole), 20 μM amino acid mix minus Met, 20 units RNAsin in a total volume of 12.5 μl. In some experiments 1 Eq microsomes (Promega) was also included in the translation reaction. Incubation was at 30° C. for 1 hr.

Following translation, aliquots were removed for further treatment or analysis by SDS-polyacrylamide gel electrophoresis.

To identify whether the synthetic or heterologous natural signal peptides attached to the NH$_2$-terminal end of PAI-2 were functioning and processed correctly, the reticulocyte lysate translation mix was supplemented with dog pancreatic microsomal vesicles (Promega). Microsomes are generated from endoplasmic reticulum (ER) and allow signal peptide cleavage, protein translocation and core glycosylation events to be studied. Any core carbohydrates added to asparagine residues in PAI-2 molecules on translocation across the ER are removed by digesting the translation products with endoglycosidase H. The extent of translocation of a protein across the membrane is assessed by incubating the processed in vitro translation products with proteinase K. Any of the protein not fully translocated into the lumen of the microsomal vesicle is liable to be digested by proteinase K.

Endoglycosidase H digests were carried out by incubating 2 μl translation mix plus 4 μl RIPA buffer (1% Triton X100, 1% sodium deoxycholate, 0.1% SDS, 150 mM NaCl, 50 mM Tris-Cl pH 7.5, 5 mM EDTA) plus 1 μg aprotinin with 2 mUnits Endo H (Boehringer Mannheim) in a 10 μl reaction at 37° for 1 hr.

Proteinase K digests were carried out as follows. 2 μl translation mix plus 5 μl phosphate buffered saline plus 0.1 μg/μl proteinase K were incubated on ice for 60 mins. In some reactions 1 μl 1% Triton X-100 was included. Samples were boiled in 1.5% SDS, 1% 2-mercaptoethanol before electrophoresis on 10% polyacrylamide-SDS gels.

Figure 4A:
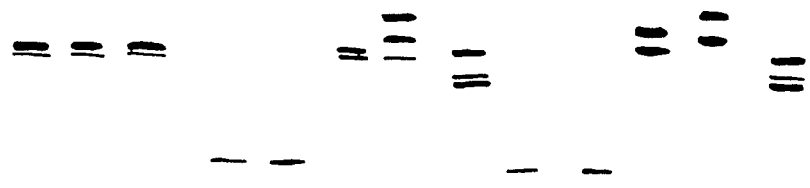
FIG. 4A–B shows the products of the PAI-2 gene and signal variants translated in a cell-free system and electrophoresed through an SDS-PAG.
Figure 4B:

FIGS. 4A and 4B show the results of typical cell-free translation experiments. The autoradiogram in FIG. 4B shows that the primary translation product of the native PAI-2 gene (pBTA821) consists of a 43,000 Mr molecule (FIG. 4B lane b). It is not translocated into the microsomes since proteinase K digests the product whether microsomes were present (FIG. 4B lane d) or absent (FIG. 4B lane a). Also the native product is not glycosylated since digestion with endoglycosidase H (FIG. 4A lane d) has no effect on the migration of the Mr 43,000 product. This 43,000 Mr product was also immunoprecipitated with anti-PAI-2 monoclonal antibody. In contrast the primary translation products of both signal-PAI-2 variants (pBTA822 and pBTA823, see FIG. 4A, lanes g and l) have higher molecular weights (44,000–45,000) than the native PAI-2 (FIG. 4A, lane b) due to the additional signal peptide. When microsomes are included in the reaction, the translation products of pBTA822 and pBTA823 migrate more slowly (Mr 45,000–46,000) due to processing of the signal and addition of carbohydrates. There are two distinct products (44,500 and 46,000 Mr) which are fully protected from digestion with proteinase K (FIG. 4B, compare lanes i and j, or o and p). Both these products are reduced in size when digested with Endo H (FIG. 4A, compare lanes h and i or m and n) to 43,000 and 41,000 Mr. These results indicate that the addition of either signal peptide to PAI-2 allows PAI-2 to be translocated across the endoplasmic reticulum membrane and to be glycosylated. Furthermore the added signal is cleaved off during translocation.

TRANSIENT EXPRESSION IN MAMMALIAN CELLS

For details of tissue culture techniques used see Freshney (1987). To determine whether the signals attached to PAI-2 enhanced the processing and secretion of PAI-2 from mammalian cells, the native PAI-2 and the two signal variant PAI-2 genes were placed downstream of the SV40 late promoter in the eukaryotic expression vector PSVL (Pharmacia). The construction of these vectors pBTA824, pBTA825 and pBTA826 was described above and is summarized in FIG. 3.

Plasmids pBTA824, pBTA825, pBTA826 were transfected into the monkey kidney COS cell line by the calcium phosphate method (Spandidos and Wilkie, 1984). Approximately $6 \times 10^5$ cells were seeded into a 100mm culture dish in 10 ml Dulbecco's modified Eagle medium supplemented with 10% (v/v) foetal calf serum, 2 mm glutamine, 50 IU ml penicillin and 50 µg/ml streptomycin. Ten micrograms of CsCl purified DNA was precipitated with calcium phosphate and added to the cells. After 4 hrs the cells were treated to a glycerol shock and cultured in the above medium for about 42 hrs.

Figure 5:
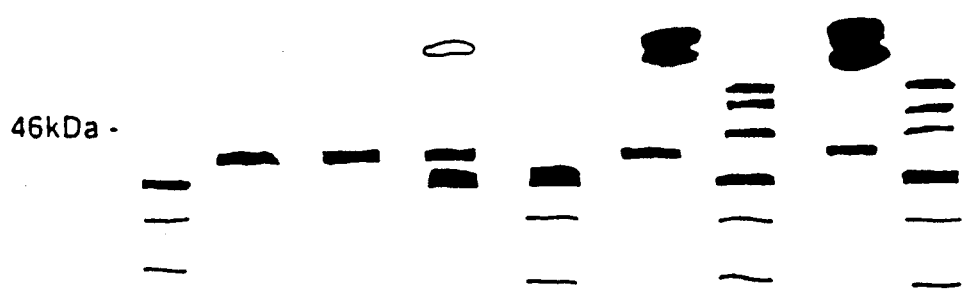
FIG. 5 shows expression of PAI-2 gene and signal variants in transfected mammalian cells. Aliquots of the medium were immunoprecipitated with an anti-PAI-2 antibody and precipitates run on an SDS-PAG.

To assay for expression and secretion of PAI-2 from these cells, the medium was removed about 42 hrs after glycerol shock and replaced with Eagles minimal essential medium lacking methionine (Flow) supplemented with 100 µCi/ml $^{35}$S-methionine (Amersham SJ1015 1000 Ci/mmole). After 4 hrs of metabolic labelling the medium was collected for analysis and the cells washed with an ice cold phosphate buffered saline solution, harvested and lysed. Cells were lysed in 1% Triton X100, 0.1% SDS, 150 mM NaCl, 50 mM Tris-Cl pH7.5, 5 mm EDTA. PAI-2 was immunoprecipitated from aliquots of medium and cell lysates by incubating with 25 µg/ml anti-PAI-2 mouse monoclonal antibody (MAI-21, Biopool) at 4° C. overnight in a solution containing 1% Triton X100 and 10 µg/mi. aprotinin. Antibody-PAI-2 complexes were extracted with 20 µl anti-mouse IgG-agarose beads (Sigma) in 10 mM sodium phosphate pH 7.2, 0.5M NaCl. The PAI-2 was eluted from the beads with 0.15 M NaCl/0.1 M glycine pH 2.4, analysed by SDS-polyacrylamide gel electrophoresis under reducing conditions and visualized by autoradiography as shown in FIG. 5. Some cells were incubated with 5 µg/ml tunicamycin for 18 hrs prior to and during the labelling, to prevent N-linked glycosylation.

Recombinant PAI-2 is seen in FIG. 5, lanes f and h as a broad band of Mr 53,000–60,000. These are samples of medium from cells transfected with the synthetic signal-PAI-2 gene (pBTA825) and α-1-antitrypsin signal-PAI-2 gene (pBTA826) respectively. The medium from mock transfected cells (i.e. no added DNA) and from cells transfected with the vector alone (PSVL) contain no 60,000 Mr material (lanes b and c). However a small amount of 60,000 Mr material and a larger amount of 43,000 Mr material is present in the medium from pBTA824 transfected cells (lane d). The 43,000 Mr material appears not to be glycosylated (compare lanes d and e).

Clearly the addition of the signal peptide to the PAI-2 molecule greatly enhances the secretion of the 60,000 Mr glycosylated form from COS cells.

The biological activity of the 58–60,000 Mr forms of PAI-2 were determined by a urokinase (uPA) binding assay. Urokinase (45 IU Low Mol Wt, American Diagnostics) was added to an aliquot of medium containing $^{35}$S-labelled PAI-2 from transfected COS cells. Binding was allowed to proceed at room temperature for 90 mins. The uPA-PAI-2 complexes were immunoprecipitated from the reaction using goat anti-PAI-2 antibodies or rabbit anti-uPA serum and a solid phase 2nd antibody. Material was eluted from the immunobeads by boiling in a buffer containing 1.5% SDS and 1% (v/v) 2-mercaptoethanol and then analysed under reducing conditions by SDS-PAGE.

FIG. 6 shows the results of such an experiment. The Mr 43,000 nonglycosylated PAI-2 released from COS cells transfected with the native gene (FIG. 6, lane c) forms a Mr 76,000 complex when uPA is added (FIG. 6, lane d). The 58–60,000 glycosylated PAI-2 secreted from COS cells transfected with either of the signal-PAI-2 constructs also binds uPA and a complex of Mr around 89,000 is formed (FIG. 6, lanes f and h). This complex is immunoprecipitable with both anti-PAI-2 and anti-uPA antibodies. This demonstrates that the 58–60 kD glycosylated and secreted form of PAI-2 is biochemically active.

CARBOHYDRATE ATTACHMENT

To determine the nature of the carbohydrates attached to the 60,000 Mr PAI-2, the material secreted from COS cells was digested with a variety of endoglycosidases (see Glycanalysis Systems Manual from Genzyme Corp. USA). The 60,000 Mr form was immunoprecipitated from the medium of cells transfected with pBTA826 as described above. Aliquots of this material were digested as follows.

(a) 1% Triton X-100, 1% Na deoxycholate, 0.1% SDS, 150 mm NaCl, 50 mM Tris-Cl pH 7.5, 5 mM EDTA, 2 mUnits Endoglycosidase H (Boehringer Mannheim) at 37° C. for 1 hr.

(b) 1% Triton X-100, 0.1% SDS, 10 mM Na phosphate pH7.2, 400 munits glycopeptidase F (Boehringer Mannheim) at 37° for 1 hr.

(c) 1% triton X-100, 0.1% SDS, 10 mM D-galactono γ lactone, 10 mM Na phosphate pH7.2, 1 m Unit neuraminidase and/or 1 mU endo-α-N-acetylgalactosaminidase (Boehringer Mannheim) at 37° for 1 hr.

Figure 9:
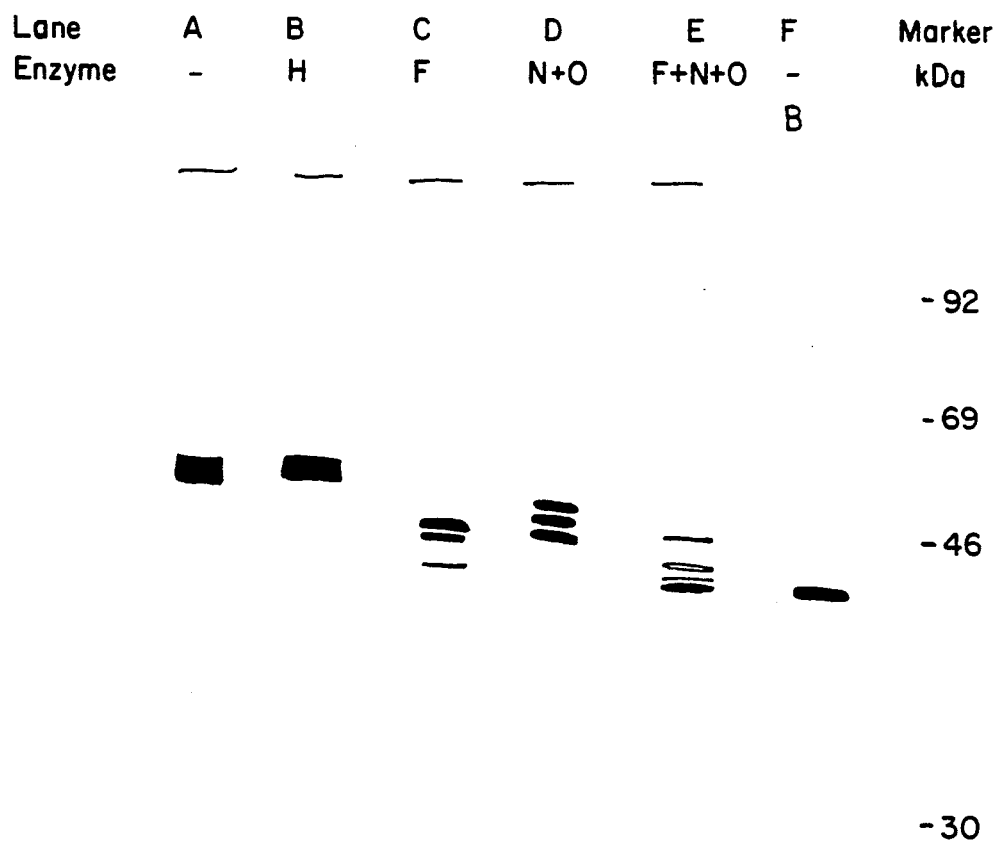
FIG. 9 shows the digestion of the 60,000 Mr PAI-2 secreted from transfected COS cells with various glycosidases. The products were separated by SDS-PAGE.

After digestion the products were analysed by SDS-PAGE and autoradiography. Digestion with endo H had no effect on the mobility of 60,000 Mr PAI-2 (FIG. 9, lane B) indicating that any N-linked carbohydrate contained complex sugars added in the Golgi. However digestion with glycopeptidase F (which removes all N-linked carbohydrate) reduced the 60,000 Mr material to a doublet of Mr 49,000 and 50,000 (FIG. 9, lane C). These forms have higher molecular weights than unglycosylated PAI-2 (43,000 Mr). The possibility that some O-linked carbohydrate was also attached to PAI-2 was confirmed by digesting the 60,000 Mr form with glycopeptidase F, neuraminidase and endo-α-N-acetyl galactosaminidase (which removes O-linked sugars). The combination of these three enzymes reduced the 60,000 Mr form to a 43,000 Mr form (FIG. 9, lane E), the size of unglycosylated PAI-2 (FIG. 9 lane F).

NH$_2$ TERMINAL DETERMINATION

To determine the NH$_2$- terminal residue of the secreted 60,000 Mr form of PAI-2, $^{35}$S-methionine or $^3$H-leucine labelled material secreted from transfected COS cells were subjected to immunoprecipitation using the anti-PAI-2 mouse monoclonal antibody (MAI-21, Biopool) as described above.

Figure 10A:
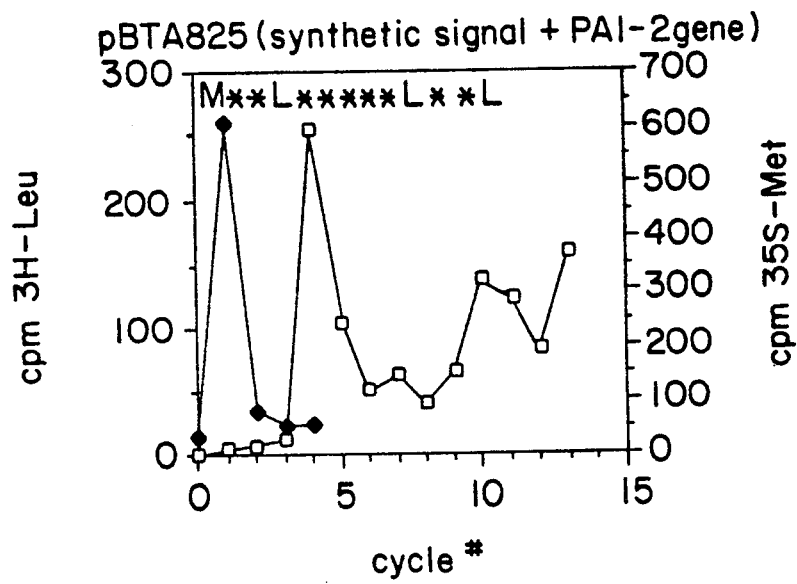
FIG. 10A–B shows the peaks of radioactivity released during repeated cycles of Edman degradation on labelled 60,000 Mr PAI-2 secreted from COS cells transfected with:
  A: PBTA 825 (contains PAI-2 gene with synthetic signal)
  B: PBTA 826 (contains PAI-2 gene with alpha-1 antitrypsin signal)
Figure 10B:
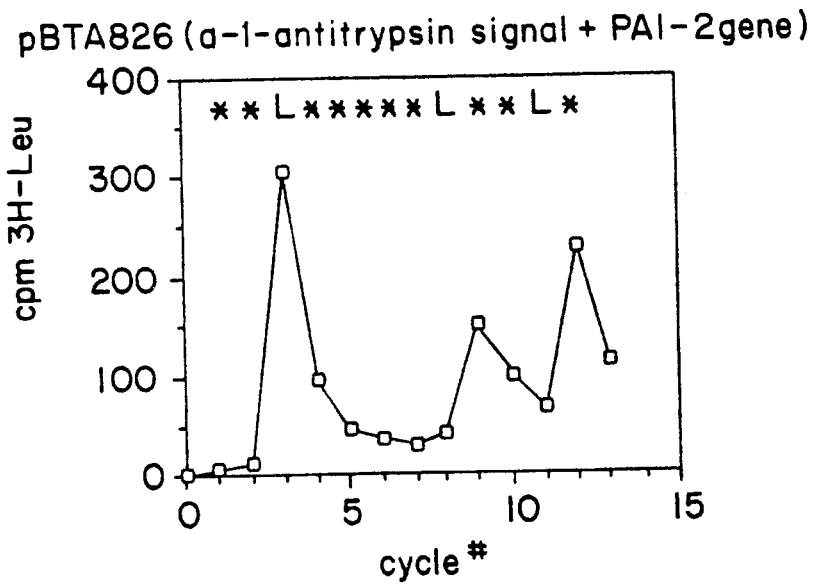

An aliquot of the $^{35}$S-Met labelled PAI-2 recovered from the medium was analyzed by SDS-polyacrylamide gel electrophoresis and shown to contain 60,000 Mr material. The $^{35}$S-Met labelled 60,000 Mr PAI-2 was applied to the Applied Biosystems Protein Sequencer (Model 470A) and subjected to repeated cycles of Edman degradation (see Instruction Manual for Protein Sequencer). Fractions from each cycle were collected and counted in a Liquid Scintillation Counter. The results of this analysis (FIG. 10A) indicated that the NH$_2$ terminal residue of the 60,000 Mr PAI-2 secreted from COS cells transfected with pBTA825 is Met.

The $^3$H-leu labelled 60,000 Mr forms of PAI-2 were electrophoresed through an SDS-polyacrylamide gel and transferred to Pro Blot PVDF membrane by electroblotting (Matsudaira, 1987). A fragment of the membrane containing the 60 kDa PAI-2 was excised and then applied to the Protein sequencer and sequenced as above with modifications to the Sequencer program as described by Speecher, 1989.

The results (FIGS. 8A, 8B) indicated that the 60,000 Mr PAI-2 secreted from COS cells transfected with pBTA825 has Leu residues at positions 4, 10 and 13, i.e. the synthetic signal peptide has been cleaved to leave PAI-2 with Met at its NH$_2$- terminus. However, the 60,000 Mr PAI-2 secreted from COS cells transfected with pBTA826 has Leu residues at positions 3, 9 and 12. This indicates that the alpha-1-antitrypsin signal has been cleaved off leaving a glycosylated PAI-2 molecule with Glu at its NH$_2$-terminus.

Figure 7:
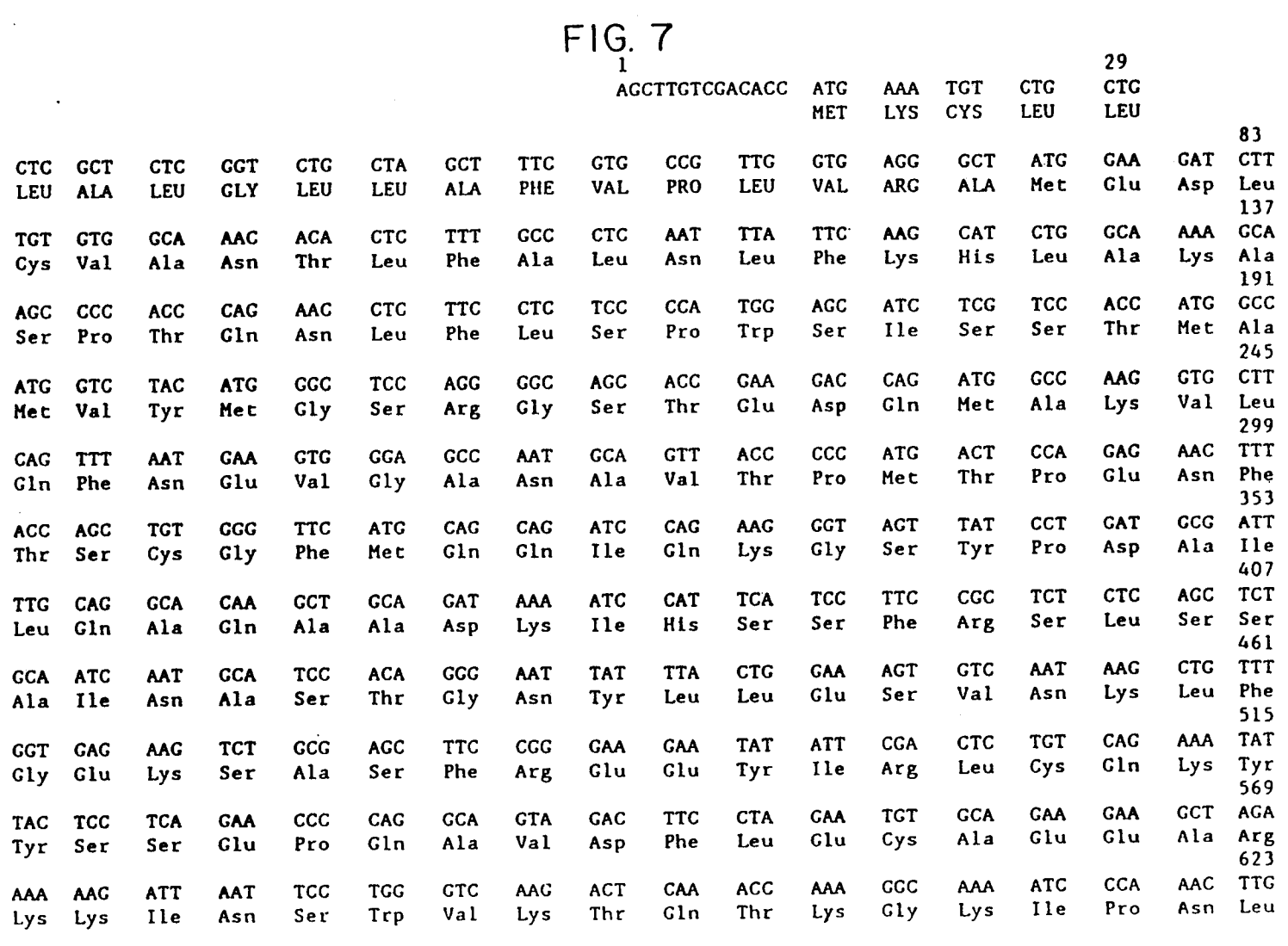

These results demonstrate that the signal peptides have been cleaved during processing of PAI-2 through the cell, that cleavage of the synthetic signal peptide occurs between Ala 19 and Met 20 (FIG. 7), that cleavage of the alpha-1-antitrypsin signal occurs between Ala 24 and Glu 25. The 60,000 Mr PAI-2 secreted from COS cells transfected with pBTA825 is 415 amino acid residues. However, the 60,000 Mr PAI-2 secreted from COS cells transfected with pBTA826 contains 414 amino acid residues.

STABLE EXPRESSION IN MAMMALIAN CELLS

For details of tissue culture techniques used see Freshney (1987). The stable expression of PAI-2 genes integrated into host cell genomes was investigated in various cell lines. Cell line CHO-KL (ATCC CCL 61) is derived from a Chinese hamster ovary cell. Cell line U937 is the human monocute-derived cell which expresses PAI-2 and from which the PAI-2 gene was isolated (Antalis et al, 1988). Other host cells for the expression of PAI-2 include the hamster kidney cell line BHK-21 (ATCC CCL10), the human kidney cell line 293 (ATCC CRL1573), the human epithelial cell-derived line HeLa S3 (ATCC CCL2.2), and the human monocute cell line HL60 (ATCC CCL 240) and insect cell lines derived from Spodoptera frugiperda (Sf9, ATCC CRL1711) and Bombyx mori (Maeda et al, 1984).

Figure 3A:
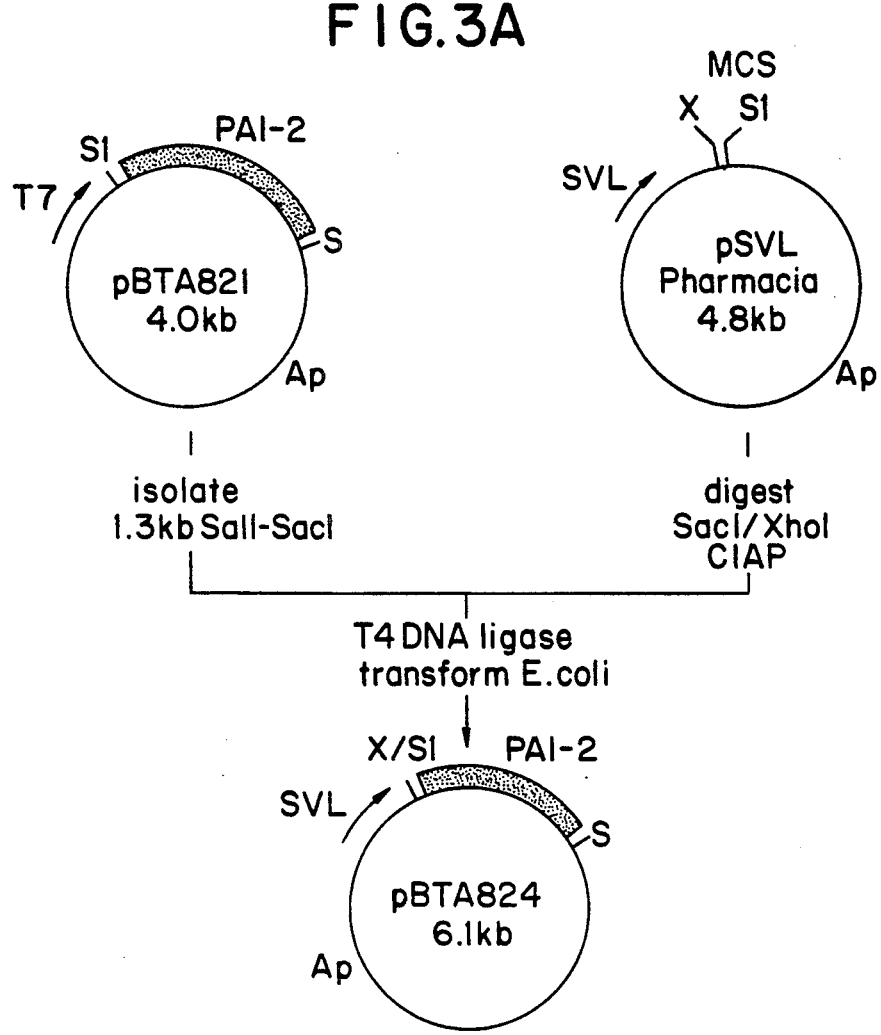
FIG. 3A–D shows construction of mammalian cell expression vectors:
  A: PBTA 824 containing PAI-2 gene without signal
  B: PBTA 825 and PBTA 827 containing PAI-2 gene with synthetic signal
  C: PBTA 826 and PBTA 828 containing PAI-2 gene with α-1-antitrypsin signal
  D: PBTA 839 containing PAI-2 gene with synthetic signal
Figure 3B:
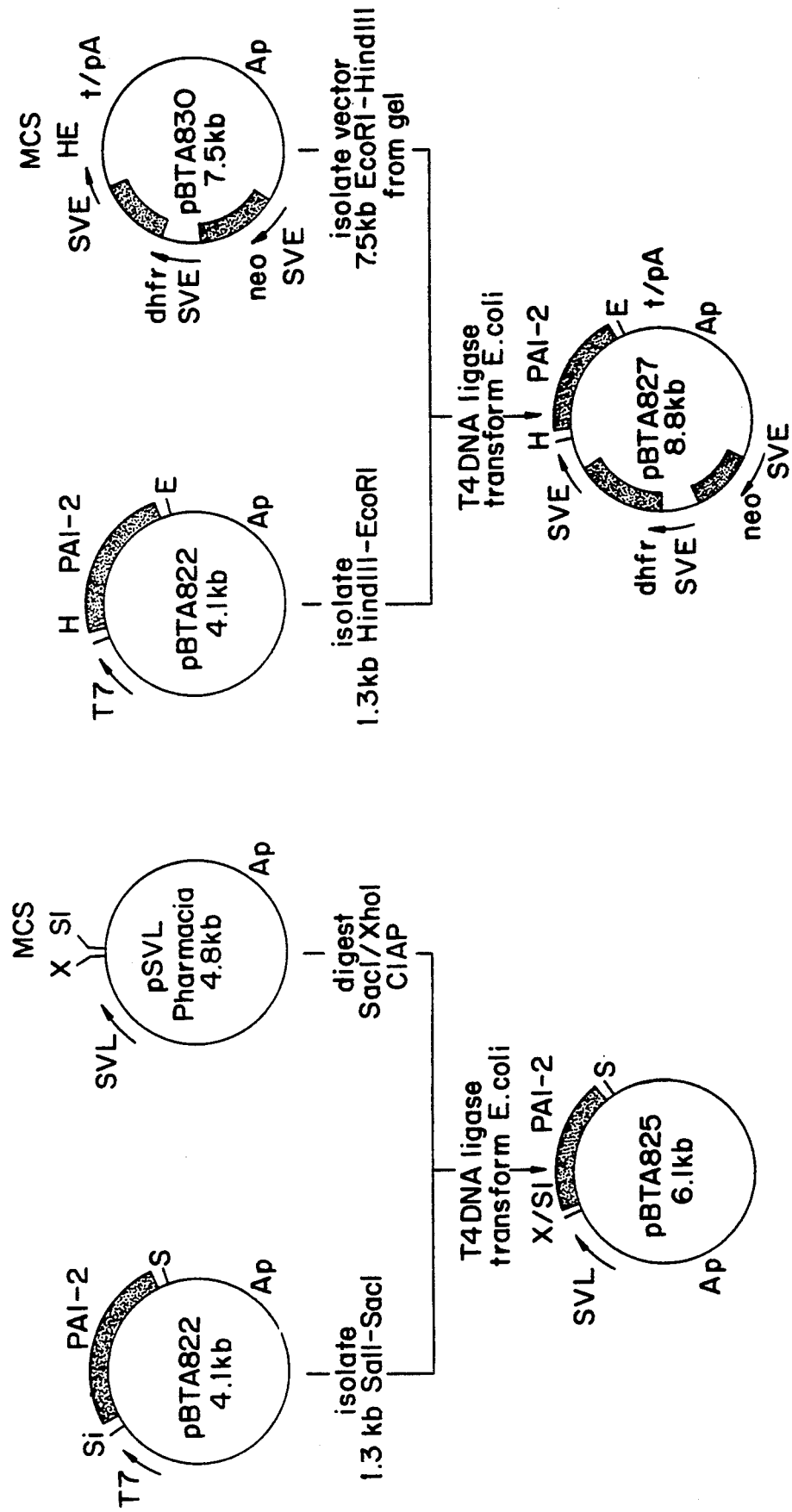
Figure 3C:
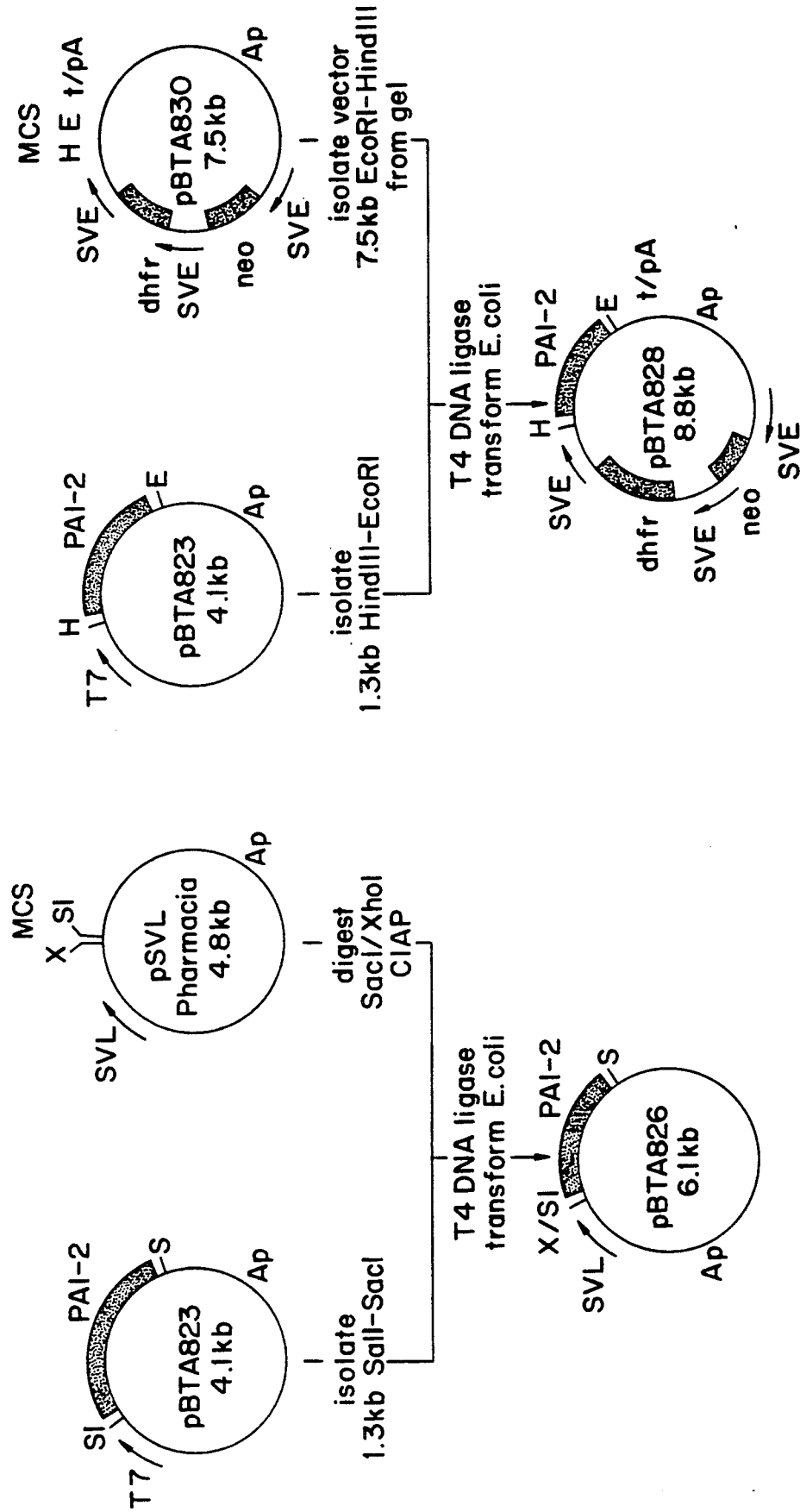

The PAI-2 genes with added signal sequences were inserted into the vector pBTA830 which contains the mouse dhfr gene and the gene conferring resistance to the aminoglycoside antibiotic, G418 (FIGS. 3B and 3C). The resultant plasmids pBTA827, pBTA828, were transfected into the above cell lines by the calcium phosphate method described, using 2 μg plasmid DNA/2×10$^5$ cells and a total of 3×10$^6$, or by electroporation. Electroporation was carried out using 1 μg linearized plasmid DNA/10$^7$ cells suspended in phosphate buffered saline/272 Mm sucrose, pH 7.4, at 4° C., and pulses of 150-300 V at a capacitance of 250 μFD (Ausubel et al, 1987). The apparatus used was a Bio-Rad Gene Pulser.

The selection of transfectants of the CHO-K1 cell line was achieved in the nucleoside-free alpha modification of Eagles medium (αMEM) containing 2% (v/v) dialysed foetal bovine serum and 400 μg/ml G418. This regime selected for both the dhfr and the G418-resistance genes present in the PAI-2 encoding plasmid. Selection of transfectants of other cell lines was done with αMEM or RPMI 1640 medium (CytoSystems) containing 2-10% foetal bovine serum and 400 μg/ml G418. After selection, the PAI-2 genes were amplified along with cotransfected (and host) dhfr genes by exposure of the cultures to increasing levels of methotrexate from 0.1 μM to 10 μM over three months as described by Zettlemeisl et al. (1987).

The resultant transfected cultures with stably integrated, amplified PAI-2 genes were examined for the secretion of PAI-2 into serum-free culture medium by an ELISA (Biopool, Sweden) performed according to the manufacturers instructions. Different cultures (pools) containing cells originating from many hundreds of transfection events were assayed by ELISA and the pools with the highest PAI-2 expression were chosen. The identity of the molecular weight forms of PAI-2 secreted from these cultures was verified by immunoprecipitation of culture supernatants and SDS-polyacrylamide gel electrophoresis as described above. High molecular weight, glycosylated forms of PAI-2 are produced by representative cultures as shown in FIG. 11. The biological activity of the secreted forms of PAI-2 can be determined using a coupled photometric assay for plasminogen activator(Coleman and Green, 1981). The first step of the reaction involves the activation of purified plasminogen to plasmin by uPA. The activity of plasmin is then detected by the formation of a yellow thiophenolate anion. PAI-2 activity is expressed in Ploug units/ml.

Finally, clones of individual cells from the highest expressing cell pool are isolated by the limiting dilution method (Freshney, 1987). Cell colonies are assayed for PAI-2 by transferring them to nylon filters as described by Raetz et al. (1982) and detecting PAI-2 by Western blot analysis. Colonies with maximal PAI-2 expression are isolated, re-cloned, and the secreted forms of PAI-2 verified as described above.

The stable expression of PAI-2 genes integrated into host genomes was investigated further in various cell lines including CHO,DG44 and Vero. Cell line DG44 is a derivative of the Chinese hamster ovary cell CHO-K1 and contains a deletion of the gene for dihydrofolate reductase (dhfr. Urlaub et al., 1986). Vero is derived from an African green monkey kidney cell (ATCC CCL81).

Figure 3D:
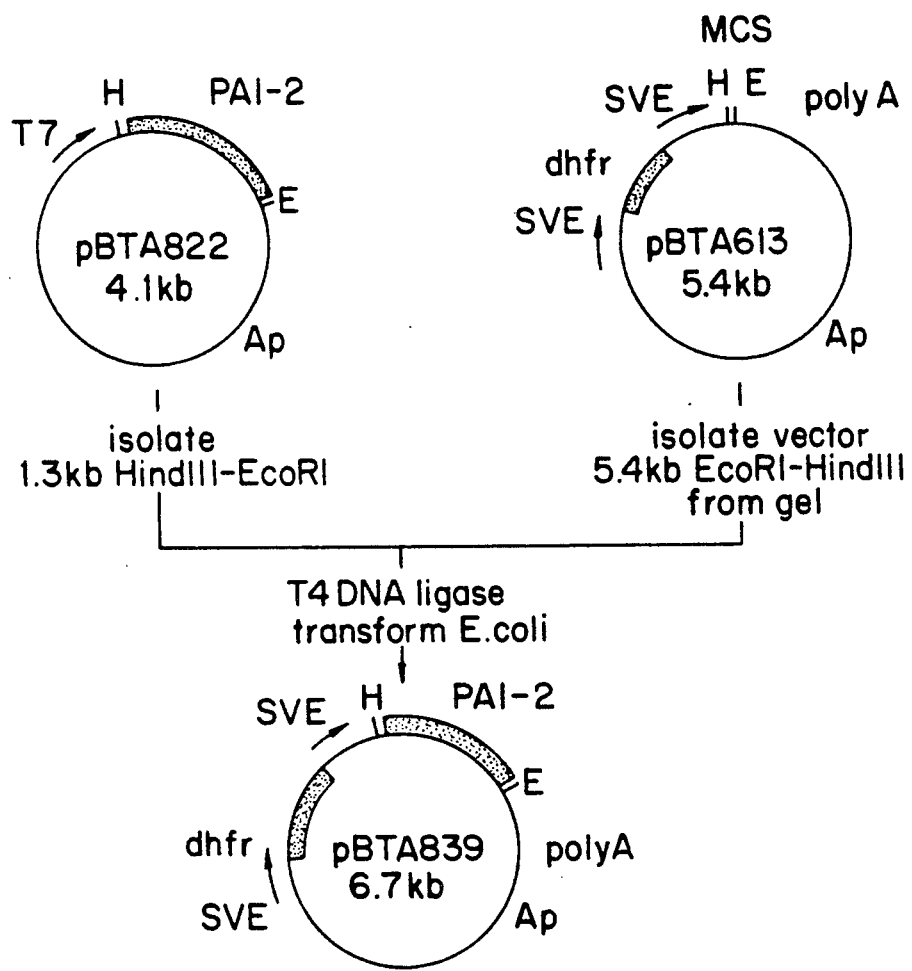

The PAI-2 gene with added signal sequence was inserted into the vector pBTA613 which contains the mouse dhfr gene (FIG. 3D). The resultant plasmid pBTA839 was transfected into the above cell lines by the calcium phosphate method described, using 10 μg plasmid DNA/2×10$^5$cells and a total of 2×10$^6$cells, or by electroporation. Electroporation was carried out as described by Barsoum (1990) using the Bio-Rad Gene Pulser.

The selection of transfectants of cell line DG44 was achieved in the nucleoside-free medium αMEM (CytoSystems) containing 2% (v/v) dialysed foetal bovine serum and 0.1–0.5 μM methotrexate. The selection of transfectants of Vero cells was done in the same medium. This procedure selects for transfectants with an elevated number of copies of integrated plasmid. After selection, the PAI-2 genes were amplified along with cotransfected (and host) dhfr genes by exposure of the cultures to increasing levels of methotrexate up to 10 μM as described by Zettlemeisl et al (1987). The resultant transfected culture with stably integrated, amplified PAI-2 genes are examined for the secretion of PAI-2 into the serum-free culture medium by an ELISA for PAI-2 (Biopool, Sweden) performed according to the manufacturers instructions. Single colonies arising from the transfection and pools containing cells originating from many thousands of transfection events are assayed by ELISA and those with the highest PAI-2 expression are chosen. The identity of the molecular weight forms of PAI-2 secreted from these cultures is verified by immunoprecipitation of culture supernatants and SDS-polyacrylamide gel electrophoresis as described above.

Clones of individual cells are also isolated from the highest expressing cell pool by limiting dilution method (Freshney, 1987). Cell colonies are assayed for PAI-2 by transferring them to nylon filters as described by Raetz et al. (1982) and detecting PAI-2 by Western blot analysis. Colonies with maximal PAI-2 expression are isolated, re-cloned, and the secreted forms of PAI-2 verified as described above.

ABSENCE OF EFFICIENT SIGNAL SEQUENCE FROM NATIVE PAI-2

The in vitro translation experiment with microsomes has for the first time demonstrated that native PAI-2 does not contain a signal sequence that is efficiently recognized by the protein translocation machinery present in some mammalian cell extracts. This may explain the observations that PAI-2 is predominantly an intracellular protein. The little material that is secreted is often unglycosylated and may be released from the cells by an unknown mechanism which does not involve transport of PAI-2 through the normal secretory pathway of the ER and Golgi. However high mr forms of PAI-2 have also been observed; hence PAI-2 must have the capacity to translocate into the ER and Golgi (where addition of carbohydrate occurs). The signal to allow this has not been identified. Given the results with the in vitro system described above any signal in native PAI-2 must be very inefficiently recognized by the signal recognition protein. To overcome this problem, and to ensure efficient secretion of large amounts of high molecular weight forms of PAI-2 from mammalian cells we have added a signal peptide to the NH$_2$-terminus of PAI-2. Results described above show that either an artificial signal peptide or a natural signal peptide can be attached to PAI-2 to create a molecule which is translocated across the endoplasmic reticulum. The signal is cleaved and PAI-2 is processed through the secretory pathway. These high molecular weight forms of PAI-2 are glycosylated and bind to uPA.

PURIFICATION

The secreted PAI-2 is purified using established and published procedures (see International Patent Application No. PCT/AU87/00068).

INDUSTRIAL APPLICATIONS

The expression products, secreted glycosylated recombinant 60 kD PAI-2 and the 414 amino acid form of PAI-2 of the invention are of use as diagnostic or therapeutic substances in the fields of:

therapy, prophylaxis and diagnosis of inflammatory disease;

therapy, prophylaxis and diagnosis of cancer metastasis and proliferation;

therapy of transplant and placenta rejection crises and graft-versus-host reactions;

therapy and diagnosis of autoimmune diseases and diseases associated with excessive oxygen radical production;

therapy and prophylaxis of wound and bone healing disorders, tissue damage during or after acute reperfusion, and subarahnoidal bleeding disorders;

as topical medicaments for promoting fibrin adhesion, promoting healing of wounds and burns;

treating asthma and treating or preventing diseases associated with high leukocyte activity; and suppression of the monocute-macrophage system.

Specific examples from the above classes of disease include:

rheumatoid arthritis
osteoarthritis
colitis ulcerosa
systemic lupus erythematosus
multiple sclerosis
psoriasis
pemphigus
corneal and duodenal ulceration
purpura
periodontitis
muscular dystrophy

REFERENCES

Antalis, T. M., Clark, M. A., Barnes, T., Lehrbach, P. R., Devine, P. L., Schevzov, G., Goss, N. H., Stephens, R. W. and Tolstoshev, P. (1988). Proc. Natl. Acad. Sci. USA 85, 985–989.

Ausubel, F. M., Brent, R., Kingston, R. E., Moore, D. D., Seidman, J. G., Smith, J. A. and Struhl, K. (1987). *Current Protocols in Molecular Biology*, Chap 9, Wiley Interscience, PA, USA.

Barsoum, J. (1990) Introduction of stable high-copy-number DNA into Chinese hamster ovary cells by electroporation. DNA and Cell Biol. 9 293–300.

Beck, E., Ludwig G., Averswald, E.-A., Reiss, B. and Schaller, H. (1982) Gene 19, 327–336.

Belin, D., Wohlwend, A., and Vassalli, J. D. (1989) Abstracts of the Second International Workshop on the Molecular and Cellular Biology of Plasminogen Activation, Brookhaven National Laboratory, Long Island, N.Y., April 1989.

Belin, D., Wohlwend, A., Schleuning, W-D, Kruithof, E. K. O. and Vassalli, J. D. (1989) EMBO Journal 8:3287–3294.

Birnboim, H. C. and Doly, J. (1979). A rapid alkaline extraction procedure for screening recombinant plasmid DNA. Nucleic Acids Res. 7, 1513.

Botterman, J. and Zabeau, M. (1985). Gene 37, 229–239.

Coleman, P. L. and Green, G. D. J. (1981). Methods in Enzymology 80, 408–414.

Freshney, R. I. (1987). *Culture of Animal Cells* 2nd ed., pp-137–139. Alan R. Liss, Inc., New York.

Genton, C., Kruithof, E. K. O. and Schleuning, W-D (1987). Phorbol ester induces the biosynthesis of glycosylated and nonglycosylated plasminogen activator inhibitor 2 in high excess over urokinase-type plasminogen activator in human U-937 lymphoma cells. J. Cell. Biol. 104, 705–712.

Gottesman, M. E., Adhya, S. and Das, A. (1980). Transcription anti-termination by bacteriophage λ N gene product. J. Mol. Biol. Jft, 57–75.

Hanahan, D. (1985). Techniques for transformation of E. coli. in DNA Cloning Volume 1, D. M. Glover (ed.) IRL Press, Oxford pp. 109–135.

Hiebert, S. W. and Lamb, R. A. (1988). Cell surface expression of glycosylated, nonglycosylated and truncated forms of a cytoplasmic protein pyruvate kinase. J. Cell. Biol. 107, 865–876.

Kruithof, E. K. O., Vassalli, J-D., Schleuning, W-D., Mattaliano, R. J. and Bachman, F. (1986). Purification and characterization of plasminogen activator inhibitor for the histiocytic lymphoma cell line U-937. J. Biol. Chem. ZU, 11207–11213.

Lecander, I. and Astedt, B. (1986). Isolation of a new specific plasminogen activator inhibitor from pregnancy plasma. Brit. J. Haemot., 62, 221–228.

Maeda, S., Kawai, T., Obinata, M., Fujiwara, H., Horiuchi, T., Saeki, Y., Sato, Y. and Furusawa (1984). Production of human α-interferon in silkworm using a baculovirus vector. Nature 592–594.

Maniatis, T., Fritsch, E.F. and Sambrook, J. (eds) (1982). Molecular Cloning a laboratory manual, CSH Laboratory, Cold Spring Harbor.

Matsudaira, P. (1987) J. Biol. Chem. 261. 10035–10038.

Medcalf, R. L., Van den Berg, E. and Schleuning W-D (1988). Glucocorticoid-modulated gene expression of tissue-and urinary-type plasminogen activator and plasminogen activator inhibitor 1 and 2. J. Cell. Biol. 106, 971–978.

Morein, et al (1984) Nature 308 457–460.

Ny, T., Lawrence, D. and Astedt, B. (1988). Fibrinolysis Abstract Volume 2 Supplement 1, No. 21, p.11

Ny, T., Hansson, L., Lawrence, D., Leonardsson, G. and Astedt, B. (1989) Fibrinolysis 3: 189–196.

Raetz, C. R. H., Wermuth, M. M., McIntyre, T. M. Esko, J. D. and Wing, D. C. (1982). Proc. Natl. Acad. Sci. USA 79, 3223–3227.

Soberon, X., Covarrubias, L. and Bolivar, F. (1980). Gene 9, 287–305.

Spandidos, D. A. and Wilkie, N. M. (1984). Expression of exogenous DNA in mammalian cells. in Transcription and Translation, B. D. Hames and S. J. Higgins (eds.), IRL Press, Oxford, PP 1–48.

Speicher, D. W. (1989) in "Techniques In Protein Chemistry" T. E. Hugli (ed) pp 24–35.

Subramani, S., Mulligan, R. and Berg, P. (1981). Mol. Cell. Biol. 1, 854–864.

Urlaub, G., Mitchell, P. J., Kas, E., Chasin, L. A., Funanage, V. L., Myoda, T. T. and Hamlin, J. (1986). Effect of gamma rays at the dihydrofolate reductase locus: deletions and insertions. Som. Cell Mol. Genet. 12, 555–566. Urlaub, G. and Chasin, L. A. (1980). Isolation of Chinese hamster cell mutants deficient in dihydrofolate reductase activity. Proc. Natl. Acad. Sci. USA 77, 4216–4220.

von Heijne, G. (1986). A new method for predicting signal sequence cleavage sites. Nucleic Acids Research, 14, 4683–4690.

Yanisch-Perron, C., Vieira, J., and Messing, J. (1985). Improved M13 phage cloning vectors and host strains:nucleotide sequences of the M13mpl8 and pUC19 vectors. Gene 31 103–119.

Ye, R. D., Wun, T-C and Sadler, J. E. (1988). Mammalian protein secretion without signal peptide removal:biosynthesis of plasminogen activator inhibitor-2 in U937 cells; J. Biol. Chem., 263, 4869–4875.

Zettlmeisl, G., Ragg, H., and Karges, H. E. (1987). Expression of biologically active antithrombin III in Chinese hamster ovary cells. Bio/Technology 5, 720–725.

International Patent Application PCT/AU85/00191.
International Patent Application PCT/AU87/00068.
International Patent Application PCT/AU87/00107

---

We claim:

1. A process for the preparation of recombinant, glycosylated, secreted PAI-2 or recombinant, glycosylated, secreted PAI-2 without its N-terminal methionine, which process comprises:
   providing a construct comprising a first polynucleotide molecule encoding PAI-2 or PAI-2 without its N-terminal methionine;
   attaching a polynucleotide molecule encoding a transient signal sequence directly to the 5′ end of the first polynucleotide molecule, such that the resulting hybrid protein expressed from the construct will consist of said transient signal sequence attached directly to the NH2-terminal of said PAI-2 or PAI-2 without its N-terminal methionine; and
   expressing the construct in a eukaryotic host cell, wherein said transient signal sequence is MKCLLLALGLLAFVPLVRA (SEQ ID NO: 1).

2. A polynucleotide construct encoding a transient signal peptide attached directly to the NH2-terminal methionine or the NH2-terminal glutamic acid of PAI-2, wherein said transient signal sequence is MKCLLLALGLLAFVPLVRA (SEQ ID NO: 1).

3. A polynucleotide construct according to claim 2 wherein the construct is a DNA molecule.

4. A recombinant DNA molecule comprising a vector DNA and a DNA molecule according to claim 3.

5. A recombinant DNA molecule according to claim 4 wherein said vector DNA is plasmid DNA.

6. A recombinant DNA molecule according to claim 5 wherein said plasmid is selected from:
   pGEM4Z, pSVL, pBTA613, pBTA830 and baculovirus transfer vectors.

7. A transformed host cell transformed by a recombinant DNA molecule according to claim 4.

8. A transformed host cell according to claim 7 wherein said host cell is selected from monkey kidney COS cells, the monkey kidney cell line Vero, Chinese hamster ovary cells, the human histiocytic lymphoma U937 cell line, a derivative of CHO-K1 cells, DG-44, the hamster kidney cell line BHK-21, the human kidney cell line 293, the human epithelial cell derived line HeLa 23, the human monocyte cell line HL60 and cell lines derived from the insects *Spodoptera frugiperda* and *Bombyx mori*.

9. A process for preparing glycosylated PAI-2 or glycosylated PAI-2 without its N-terminal methionine, which process comprises culturing a transformed host cell according to claim 7 and separating the expression product from said host cell.

10. A process for preparing a transformed host cell, which process comprises providing a host cell competent for transformation and transformation said competent host cell with a recombinant DNA molecule according to claim 14.

11. A recombinant DNA molecule selected from pBTA822, pBTA823, pBTA825, pBTA826, pBTA827, pBTA828 and pBTA839.

* * * * *